United States Patent
Gaul et al.

(10) Patent No.: US 10,914,740 B2
(45) Date of Patent: Feb. 9, 2021

(54) DETECTION AND TREATMENT OF OF EARLY-STAGE OVARIAN CANCER

(71) Applicant: GEORGIA TECH RESEARCH CORPORATION, Atlanta, GA (US)

(72) Inventors: David Gaul, Atlanta, GA (US); Facundo M. Fernandez, Atlanta, GA (US); John Francis McDonald, Arnoldsville, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 410 days.

(21) Appl. No.: 15/757,305

(22) PCT Filed: Sep. 2, 2016

(86) PCT No.: PCT/US2016/050160
§ 371 (c)(1),
(2) Date: Mar. 2, 2018

(87) PCT Pub. No.: WO2017/040970
PCT Pub. Date: Mar. 9, 2017

(65) Prior Publication Data
US 2020/0025767 A1    Jan. 23, 2020

Related U.S. Application Data

(60) Provisional application No. 62/213,317, filed on Sep. 2, 2015.

(51) Int. Cl.
*G01N 33/574*    (2006.01)
*G01N 30/72*    (2006.01)
*G01N 33/53*    (2006.01)

(52) U.S. Cl.
CPC ....... *G01N 33/57449* (2013.01); *G01N 30/72* (2013.01); *G01N 33/57484* (2013.01); *G01N 2800/60* (2013.01)

(58) Field of Classification Search
CPC ....... G01N 33/57449; G01N 33/57407; G01N 33/574; G01N 33/53; G01N 33/50; G01N 33/48; G01N 30/72; G01N 30/62
USPC .......................................................... 436/64
See application file for complete search history.

(56) References Cited

U.S. PATENT DOCUMENTS

2012/0004854 A1 *    1/2012    Fernandez ............. G16H 50/20
702/19

OTHER PUBLICATIONS

Gaul, Highly-accurate metabolomics detection of early-stage ovarian cancer, Nature: Scientific Reports, Nov. 17, 2015, 5:16351. (Year: 2015).*

Guan, Wei, et al., Ovarian cancer detection from metabolomic liquid chromatography/mass spectrometry data by support vector machines, BMC Bioinformatics, Aug. 22, 2009, 10:259. (Year: 2009).*

(Continued)

*Primary Examiner* — Christine T Mui
(74) *Attorney, Agent, or Firm* — Troutman Pepper Hamilton Sanders LLP; Ryan A. Schneider

(57) ABSTRACT

A method of detecting serous ovarian cancer, particularly early stage serous ovarian cancer is described. The method uses up to sixteen compounds found in the blood serum of a person, and determines that changes of some portion of these sixteen compounds can determine the presence of serous ovarian cancer in a women with up to 100% accuracy, specificity, and sensitivity.

21 Claims, 6 Drawing Sheets

(56) References Cited

OTHER PUBLICATIONS

Guan, Wei, et al., Supplementary Additional Material : Additional file 1, Ovarian cancer detection from metabolomic liquid chromatography/mass spectrometry data by support vector machines, BMC Bioinformatics, Aug. 22, 2009, pp. 1-20. (Year: 2009).*

Gual et al, 10th Biennial Ovarian Cancer Research Symposium; Sep. 8-9, 2014; Seattle, WA . (Year: 2014).*

* cited by examiner

DETECTION AND TREATMENT OF OF EARLY-STAGE OVARIAN CANCER

CROSS-REFERENCE TO RELATED APPLICATIONS

This application is a U.S. National Stage of International Patent Application No. PCT/US2016/050160, filed Sep. 2, 2016, which claims the benefit of U.S. Provisional Patent Application Ser. No. 62/213,317, filed Sep. 2, 2015, entitled "METABOLOMIC DETECTION OF EARLY-STAGE OVARIAN CANCER," the entire contents and substance of which are hereby incorporated by reference as if fully set forth below.

TECHNICAL FIELD

The various embodiments of the disclosure relate generally to methods of detecting and treating ovarian cancers, particularly serous ovarian cancer, and more particularly early-stage serous ovarian cancer.

BACKGROUND

Ovarian cancer (OC) is the most lethal of all gynecological malignancies and the fifth leading cause of death among women living in the United States[1]. The disease is essentially asymptomatic until late stages when the 5-year relative survival rate is <44%[2]. If detected and treated early in its progression, the 5-year survival rate is ~90%. For this reason, considerable effort has been focused on the development of a screening test to diagnose OC early in its progression[3]. This challenge is confounded by the fact that because the disease is in low prevalence in the general population (~0.1% in USA), a screening test must attain a positive predictive value (PPV) of >10%, with a specificity ≥99.6% and a sensitivity ≥75% to be of clinical relevance in the general population[4].

The current standard screening method for OC involves trans-vaginal ultrasound and measurement of serum CA-125 levels[3]. Combined, these tests result in a positive predictive value of only 24%[5]. A recent study reports that monitoring changes in serum levels of CA-125 over time rather than reliance on a single predefined threshold level of significance can increase accuracy of detection up to 86%[6]. In addition, a variety of proteomic[7] and microarray[8] based tests are currently under development but, thus far, no assay has attained the stringent level of accuracy required to be of clinical relevance in the general population.

BRIEF SUMMARY

The various embodiments of the disclosure relate generally to processes, methods, and systems for screening blood serum as a highly discriminate, non-invasive tool for detection of ovarian cancer.

An embodiment of the disclosure can be a process for detecting serous ovarian cancer, including the steps of obtaining a patient's serum sample, measuring the concentration of each of ten or more OC metabolites in the serum sample as compared to the concentration of the same metabolites in a control serum sample, and evaluating the change in concentrations for the serous OC metabolites versus the control sample. The OC metabolites can be selected from Table 1 which provides 16 different OC metabolites. An increase in the concentration of metabolites 1 through 8 and/or a decrease for metabolites 9 through 16 can indicate a positive result for ovarian cancer.

Another embodiment of the disclosure can include the steps of calibrating the method prior to a measurement of a serum sample or multiple serum samples. The calibration can be conducted by testing a device with a calibration sample. The calibration step can include a calibration sample with at least three compounds selected from the following: cortisone, lysophatidylinositol (18:1), aspartyl-glutamic acid, 16-(6-butoxy-3-hydroxy-4,5-dimethylcyclohex-1-en-1-yl)-6,10-dihydroxy-2,6,10,14-tetramethyl hexadecanoicacid, ceramide, lysophosphatidylethanolamine (22:6), 2-hydroxyl nonanoic acid, iso-1,2-octadecanediol, 3-hydroxyl dodecanedioic acid, phosphatidylinositol (20:4/18:1), and 7,9,13-trihydroxyoctacosa-16,22-dienoic acid. In another embodiment of the disclosure, the calibration step can include a calibration sample with at least 5 compounds selected from the following: cortisone, lysophatidylinositol (18:1), aspartyl-glutamic acid, 16-(6-butoxy-3-hydroxy-4,5-dimethyl cyclohex-1-en-1-yl)-6,10-dihydroxy-2,6,10,14-tetramethyl hexadecanoicacid, ceramide, lysophosphatidylethanolamine (22:6), 2-hydroxyl nonanoic acid, iso-1,2-octadecanediol, 3-hydroxyl dodecanedioic acid, phosphatidylinositol (20:4/18:1), and 7,9,13-trihydroxyoctacosa-16,22-dienoic acid.

In an embodiment of the disclosure, the metabolite concentration can be measured by ultra-performance liquid chromatography with a mass spectrometer as the detector. The chromatographic separation of the metabolites can be conducted on a reverse phase column for 15 to 40 minutes. Additionally the chromatographic separation can be conducted using a water:alcohol gradient elution. In an embodiment of the disclosure the 16 OC metabolites can be separated using a C18 UPLC column with a methanol:water gradient elution, and the metabolite concentrations measured by mass spectrometry.

In another embodiment of the disclosure, the concentration of metabolites 1 through 8 can increase by a log base 2 value of at least 0.2 over the control sample. In another embodiment of the disclosure, the concentration of metabolites 10 through 16 decrease by a log base 2 value of at least 0.15 over the control sample. In an embodiment of the disclosure, the concentration change in metabolites of the serum sample versus the control sample can include a log base 2 increase of about 0.84 for metabolite 1, about 0.70 for metabolite 2, about 0.55 for metabolite 3, about 0.49 for metabolite 4, about 0.34 for metabolite 5, about 0.32 for metabolite 6, about 0.31 for metabolite 7, and about 0.20 for metabolite 8. In an embodiment of the disclosure, the concentration change in metabolites of the serum sample versus the control sample can include a log base 2 decrease of about 0.15 for metabolite 10, about 0.25 for metabolite 11, about 0.27 for metabolite 12, about 0.30 for metabolite 13, about 0.31 for metabolite 14, about 0.78 for metabolite 15, and about 1.43 for metabolite 16.

In another embodiment of the disclosure, the presence or absence of serous ovarian cancer can be detected with greater than 90% accuracy. Preferably the presence or absence of serous ovariance cancer is detected with greater than 90% accuracy, greater than 90% sensitivity, and greater than 90% specificity.

In another embodiment of the disclosure, the OC metabolites can include cortisone, lysophatidylinositol (18:1), aspartyl-glutamic acid, 16-(6-butoxy-3-hydroxy-4,5-dimethylcyclohex-1-en-1-yl)-6,10-dihydroxy-2,6,10,14-tetramethyl hexadecanoicacid, ceramide, lysophosphatidylethanolamine (22:6), 2-hydroxyl nonanoic acid, iso-1,2- octadecanediol, 3-hydroxyl dodecanedioic acid, phosphatidylinositol (20:4/18:1), and 7,9,13-trihydroxyoctacosa-16,22-dienoic acid.

In further another embodiment of the disclosure, metabolite 1 has an average m/z of about 552.2 and an average retention time of about 0.7 minutes on a 2.1 mm by 50 mm C-18 column with 1.7 m particle size when eluted on a gradient with a water:methanol solution of 80% to 10% from 0-15 minutes and 15-23 minutes at 10%. At the same conditions, metabolite 6 has an average m/z of about 365.3 and an average retention time of about 17 minutes. At the same conditions, metabolite 9 has an average m/z of about 429.3 and an average retention time of about 11.5 minutes. At the same conditions, metabolite 13 has an average m/z of about 451.2 and an average retention time of about 1.6 minutes. At the same conditions, metabolite 15 has an average m/z of about 129.1 and an average retention time of about 1.1 minutes.

In another embodiment of the disclosure, the serum sample can be prepared by a series of steps including: precipitating protein from a blood sample with methanol to make a supernatant and precipitate, separating the protein from supernatant by centrifugation, mixing the supernatant with water and freezing drying the sample, and reconstituting with mobile phase solution at the time of analysis.

In another embodiment of the disclosure, the control can include a serum sample from a group of patients that do not have ovarian cancer.

An embodiment of the disclosure can include a method for eliminating a patient's risk of late-stage serous ovarian cancer which includes the steps of: collecting a serum sample during a patient's health examination, measuring in the serum sample the concentration of each of ten or more of serous OC metabolites 1 through 16, comparing the concentration of the serous OC metabolites 1 through 16 to the concentration of the same metabolites in an unaffected control sample to determine the presence or absence of serous ovarian cancer, and prescribing a treatment regime for the patient.

Another embodiment of the disclosure can include determining a patient's presence or absence of serous ovarian cancer with greater than 90% accuracy. Preferably determining a patient's presence or absence of serous ovarian cancer with greater than 90% accuracy, greater than 90% sensitivity, and greater than 90% specificity.

Another embodiment of the disclosure can include a non-invasive method for treating serous ovarian cancer including the steps of: identifying the presence of serous ovarian cancer in a patient and treating the patient with a cancer chemotherapy and/or radiation without resorting to invasive surgical exploration. The steps of identifying the presence of serous ovarian cancer including: obtaining a serum sample from the patient, measuring the concentration of serous OC metabolites 1 through 16 in the patient's serum sample, and evaluating the change in concentrations for the serous OC metabolites 1 through 16 for the patient's sample versus a control sample.

In an embodiment of the disclosure, the evaluation step can identify the presence or absence of serous ovarian cancer with greater than 90% accuracy. Preferably the evaluation step can identify the presence or absence of serous ovarian cancer with greater than 90% accuracy, greater than 90% sensitivity, and greater than 90% specificity.

In an embodiment of the disclosure, the measurement step can additionally include calibrating the device prior to a measurement of a serum sample or multiple serum samples by testing the device on a calibration sample. In an embodiment of treating serous ovarian cancer, the measurement calibration sample can include at least 3 compounds selected from the group consisting of cortisone, lysophatidylinositol (18:1), aspartyl-glutamic acid, 16-(6-butoxy-3-hydroxy-4,5-dimethylcyclohex-1-en-1-yl)-6,10-dihydroxy-2,6,10,14-tetramethyl hexadecanoicacid, ceramide, lysophosphatidyl ethanolamine (22:6), 2-hydroxyl nonanoic acid, iso-1,2-octadecanediol, 3-hydroxyl dodecanedioic acid, phosphatidylinositol (20:4/18:1), and 7,9,13-trihydroxyoctacosa-16,22-dienoic acid. In an embodiment of treating serous ovarian cancer, the measurement calibration sample can include at least 5 compounds selected from the group consisting of cortisone, lysophatidylinositol (18:1), aspartyl-glutamic acid, 16-(6-butoxy-3-hydroxy-4,5-dimethylcyclohex-1-en-1-yl)-6,10-dihydroxy-2,6,10,14-tetramethyl hexadecanoicacid, ceramide, lysophosphatidylethanolamine (22:6), 2-hydroxyl nonanoic acid, iso-1,2-octadecanediol, 3-hydroxyl dodecanedioic acid, phosphatidylinositol (20:4/18:1), and 7,9,13-trihydroxyoctacosa-16,22-dienoic acid.

Another embodiment of the disclosure can include, a method of identifying candidates for chemotherapy and/or surgery to eliminate cancerous ovarian tissue including the steps of: collecting a serum sample during a patient's annual health examination, measuring in the serum sample the concentration of each of ten or more of serous OC metabolites 1 through 16, comparing the concentration of the serous OC metabolites 1 through 16 to the concentration of the same metabolites in an unaffected control sample to determine the presence or absence of serous ovarian cancer, and recommending the candidate for chemotherapy and/or surgery to eliminate the cancerous tissue.

An embodiment of the disclosure can include identifying candidates for chemotherapy and/or surgery to eliminate cancerous ovarian tissue where the presence or absence of serous ovarian cancer can be identified with greater than 90% accuracy. Preferably, the presence or absence of serous ovarian cancer can be identified with greater than 90% accuracy, greater than 90% sensitivity, and greater than 90% specificity.

DETAILED DESCRIPTION

Figure 1:
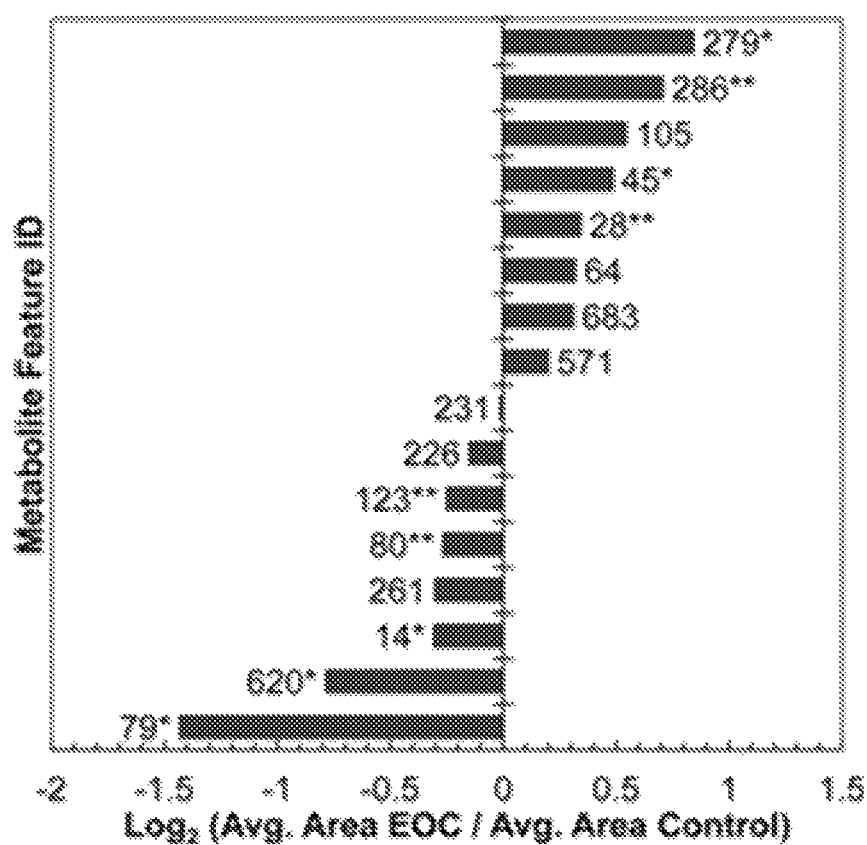
FIG. 1 illustrates the log base two ratio of peak areas for EOC versus control, in accordance with an exemplary embodiment of the disclosure.

Although preferred embodiments of the disclosure are explained in detail, it is to be understood that other embodiments are contemplated. Accordingly, it is not intended that the disclosure is limited in its scope to the details of construction and arrangement of components set forth in the following description or illustrated in the drawings. The disclosure is capable of other embodiments and of being practiced or carried out in various ways. Also, in describing the preferred embodiments, specific terminology will be resorted to for the sake of clarity.

It must also be noted that, as used in the specification and the appended claims, the singular forms "a," "an" and "the" include plural referents unless the context clearly dictates otherwise.

Also, in describing the preferred embodiments, terminology will be resorted to for the sake of clarity. It is intended that each term contemplates its broadest meaning as understood by those skilled in the art and includes all technical equivalents which operate in a similar manner to accomplish a similar purpose.

Ranges can be expressed herein as from "about" or "approximately" one particular value and/or to "about" or "approximately" another particular value. When such a range is expressed, another embodiment includes from the one particular value and/or to the other particular value.

By "comprising" or "comprising" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified.

Disclosed herein are the combined use of high- and ultra-performance liquid chromatography, high-resolution mass spectrometry (UPLC-MS) and tandem MS (MS/MS), combined with a customized support vector machine (SVM)-based learning algorithm for identification of 16 diagnostic metabolites that collectively are able to distinguish early-stage OC with 100% accuracy in our cohort. The results provide the foundation for clinically-significant diagnostic tests and evidence for the importance of alterations in lipid and fatty acid metabolism in the onset and progression of the disease.

As demonstrated by the presented work, SVM machine learning is a powerful computational tool for the identification of correlated patterns in large datasets. We have previously shown that combining this computational approach with high-resolution mass spectrometry of patient sera is a minimally invasive and highly accurate method for the detection of prostate[10] and late-stage ovarian cancers[21].

Because of the extensive genetic diversity known to exist among individual patient tumors of even the same type of OC[22], it is not surprising that it has proven extremely difficult to identify a single set of biomarkers capable of diagnosing the disease with high accuracy[23]. Although there may be multiple genetic lesions and alternative molecular pathways leading to the development of even the same type of OC, all of these mutations and pathways converge on a similar cancer phenotype. Thus, molecular features closely associated with the cancer phenotype, like metabolites, may be expected to be less variable across patients than the broader spectrum of individual mutations and disrupted pathways underlying the disease[24].

The predictive accuracy of SVM-derived biomarkers is heavily dependent upon the representative nature of the biological samples used in building the model. For this reason, the method disclosed herein included samples collected from a broad spectrum of geographic locations in the United States and Canada. The results demonstrate that this evidence-based approach to metabolic biomarker discovery is conceptually unbiased for the establishment of highly accurate biomarker panels of early-staged OC across a broad geographic area. When combined with experimental chemical identification of these diagnostic features, this approach provides valuable insight into the metabolic alterations accompanying the disease and serves as the foundation for clinically significant diagnostic tests.

One aspect of the disclosure is a method for detecting serous ovarian cancer from the blood sample of patient. The method can include the steps of obtaining the serum sample, measuring the concentration of each of ten or more of serous ovarian cancer metabolites 1 through 16, and evaluating the amount of change in the concentration for each of the serous ovarian cancer metabolites 1 through 16 versus a control sample.

The method is not merely based on the determination of if these 16 components are present. These components are present in the blood of any person, and are only a handful of hundreds of features that appear in a measurement of blood serum. As such, the term serous ovarian cancer metabolites might be misleading, because these components are not metabolites of serous ovarian cancer, but are in fact common compounds in the blood. Thus, the metabolites might also be referred to as markers, features, components or compounds. However, the disclosure does show that the change in the concentration of these 16 components in the blood serum, out of hundreds of other components, can identify the presence of serous ovarian cancer with greater than 90% accuracy, greater than 90% sensitivity, and/or greater than 90% specificity; preferably greater than 90% accuracy, greater than 90% sensitivity, and greater than 90% specificity; more preferably greater than 95% accuracy, greater than 95% sensitivity, and/or greater than 95% specificity.

The method can include the step of measuring the metabolites in the serum sample using an ultra-performance liquid chromatography with a mass spectrometer as a detector. Chromatographic separation occurs on the UPLC column, where the myriad of blood serum components can be separated and measure. The chromatographic separation of a serum sample can be conducted for 10 minutes up to 60 minutes, for 15 minutes up to 50 minutes, for 15 minutes up to 40 minutes, for 20 minutes up to 40 minutes, or for 20 minutes up to 30 minutes.

The metabolites of the serum sample can be chromatographically separated on a reverse phase column. The reverse phase column can be a C-8, C-18, or C-30 column. The reverse phase column is preferably a C-18 column. The chromatographic separation can be conducted using a mobile phase of water and alcohol, preferably water and methanol. The separation can be conducted using a gradient elution. In an embodiment, the chromatographic separation of the 16 metabolites conducted using a C18 UPLC column with a methanol:water gradient elution, and the metabolites measured by a MS detector.

The method for detecting serous ovarian cancer can include a change in the concentration of serous ovarian cancer metabolites 1 through 16 versus a control sample. A positive result for serous ovarian cancer can include an increase in the concentration of metabolites 1 through 8. A positive result for serous ovarian cancer can include a decrease in the concentration of metabolites 9 through 16. Preferably a positive result can include sample an increase in the concentration of metabolites 1 through 8 and a decrease in the concentration of metabolites 9 through 16. The increase in concentration of metabolites 1 through 8 can be by a log base 2 value of at least about 0.2 over the control sample. The decrease in the concentration of metabolites 10 through 16 can be by a log base 2 value of at least about 0.15 versus the control sample. FIG. 1 displays the fold-change of average peak areas of each discriminant feature. Positive values indicate higher levels of metabolite observed on average for EOC patients compared to control patients, while negative values indicate inverse relationship (*$p<0.05$; **$p<0.10$, Mann Whitney U test). Table 1 presents the graphical data in tabular form, including the serous ovarian cancer metabolite number, its corresponding feature ID No. from the UPLC-MS application discussed in the Examples, the m/z and retention time for that UPLC-MS data, the concentration of cancer/normal for each feature, the concentration of normal/cancer for each feature, and the log base 2 value for concentration of cancer/normal.

In some embodiments, a positive result can be obtained when the concentration change of the metabolites versus the control sample comprises a log base 2 increase of about 0.84 for metabolite 1, about 0.70 for metabolite 2, about 0.55 for metabolite 3, about 0.49 for metabolite 4, about 0.34 for metabolite 5, about 0.32 for metabolite 6, about 0.31 for metabolite 7, and about 0.20 for metabolite 8.

In some embodiments, a positive result can be obtained when the concentration change of the metabolites versus the control sample comprises a log base 2 decrease of about 0.15 for metabolite 10, about 0.25 for metabolite 11, about 0.27 for metabolite 12, about 0.30 for metabolite 13, about 0.31 for metabolite 14, about 0.78 for metabolite 15, and about 1.43 for metabolite 16.

In some embodiments, a positive result can be obtained when the concentration change of the metabolites versus the control sample comprises a log base 2 increase of about 0.84 for metabolite 1, about 0.70 for metabolite 2, about 0.55 for metabolite 3, about 0.49 for metabolite 4, about 0.34 for metabolite 5, about 0.32 for metabolite 6, about 0.31 for metabolite 7, and about 0.20 for metabolite 8, and a log base 2 decrease of about 0.15 for metabolite 10, about 0.25 for metabolite 11, about 0.27 for metabolite 12, about 0.30 for metabolite 13, about 0.31 for metabolite 14, about 0.78 for metabolite 15, and about 1.43 for metabolite 16.

TABLE 1

| Serous OC No. | Feature ID | m/z | retention time | FC C/N | FC N/C | log2(C/N) |
|---|---|---|---|---|---|---|
| 1 | 279 | 552.233 | 0.701 | 1.402 | 0.713 | 0.845 |
| 2 | 286 | 597.303 | 10.885 | 1.270 | 0.787 | 0.708 |
| 3 | 105 | 195.102 | 1.014 | 1.460 | 0.685 | 0.546 |
| 4 | 45 | 536.504 | 18.564 | 1.249 | 0.801 | 0.488 |
| 5 | 28 | 524.278 | 12.794 | 1.634 | 0.612 | 0.345 |
| 6 | 64 | 365.341 | 16.974 | 1.797 | 0.557 | 0.321 |
| 7 | 683 | 261.073 | 1.016 | 1.241 | 0.806 | 0.312 |
| 8 | 571 | 329.173 | 4.810 | 1.150 | 0.870 | 0.201 |
| 9 | 231 | 429.300 | 11.486 | 0.991 | 1.009 | −0.014 |
| 10 | 226 | 539.430 | 14.861 | 0.901 | 1.110 | −0.150 |
| 11 | 123 | 467.373 | 14.610 | 0.811 | 1.234 | −0.250 |
| 12 | 80 | 883.536 | 15.397 | 0.581 | 1.722 | −0.267 |
| 13 | 261 | 451.227 | 1.576 | 0.841 | 1.190 | −0.303 |
| 14 | 14 | 307.263 | 14.795 | 0.831 | 1.203 | −0.307 |
| 15 | 620 | 129.091 | 1.138 | 0.808 | 1.237 | −0.784 |
| 16 | 79 | 245.138 | 0.991 | 0.371 | 2.698 | −1.432 |

As part of the effort in developing the methods disclosed herein, identification and/or characterization of the serous ovarian cancer metabolites 1 through 16 was achieved. Table 2 shows the feature number, retention time, average m/z, metabolite identification and other information for each of the 16 serous ovarian cancer metabolites. (m/z=mass-to-charge ratio, min=minutes, ppm=part per million, CAS=chemical abstract service, USPTO=United States Patent and Trademark Office, HMDB=the human metabolome database, SVM=support vector machine, NA=not available). MS/MS fragmentation patterns of the 16 serous ovarian cancer metabolites is also provided in the Examples at Table 6.

TABLE 2

| Serum OC Metabolite # | Feature ID | Avg. m/z | Avg $R_T$ (min) | Ion Type | Ion Theoretical m/z | Mass Error (ppm) | Neutral Elemental Formula | Metabolite Identification [Database: #] |
|---|---|---|---|---|---|---|---|---|
| 1 | 279 | 552.2327 | 0.7 | $[M − H]^{2−}$ | 552.2335 | −1.4 | $C_{42}H_{80}N_3O_{30}$ | [NA] |
|   |   |   |   |   | 552.2342 | −2.7 | $C_{43}H_{76}N_7O_{26}$ |   |
|   |   |   |   |   | 552.2398 | −12.9 | $C_{42}H_{76}N_9O_{25}$ |   |
| 8 | 571 | 329.1733 | 4.81 | $[M − CHO − H]^−$ | 329.1753 | −6.1 | $C_{21}H_{28}O_5$ | cortisone [CAS: 53-06-5] |
| 2 | 286 | 597.3029 | 10.89 | $[M − H]$ | 597.304 | −1.8 | $C_{27}H_{51}O_{12}P$ | lysophatidylinositol(18:1) [CAS: 1246298-13-4] |
| 7 | 683 | 261.0727 | 1.01 | $[M − H]$ | 261.0723 | 1.5 | $C_9H_{13}N_2O_7$ | aspartyl-glutamic acid [CAS: 6157-06-8] |
| 10 | 226 | 539.4301 | 14.86 | $[M − H]$ | 539.4312 | −2.0 | $C_{32}H_{60}O_6$ | 16-(6-butoxy-3-hydroxy-4,5-dimethylcyclohex-1-en-1-yl)-6,10-dihydroxy-2,6,10,14-tetramethyl hexadecanoic acid [USPTO: document #20100086960][1] |
| 4 | 45 | 536.5042 | 18.56 | $[M − H]^−$ | 536.5043 | −0.2 | $C_{34}H_{67}NO_3$ | ceramide(d18:1/16:0) [CAS: 24696-26-2] |

TABLE 2-continued

| Serum OC Metabolite # | Feature ID | Avg. m/z | Avg $R_T$ (min) | Ion Type | Ion Theoretical m/z | Mass Error (ppm) | Neutral Elemental Formula | Metabolite Identification [Database: #] |
|---|---|---|---|---|---|---|---|---|
| 6 | 64 | 365.3413 | 16.97 | [M − H]− | 365.3425 | 1.2 | $C_{24}H_{46}O_2$ | [NA] |
| 5 | 28 | 524.2778 | 12.79 | [M − H] | 524.2777 | 0.2 | $C_{27}H_{44}NO_7P$ | lysophosphatidylethanolamine(22:6) [PUBCHEM: 52925132] |
| 3 | 105 | 195.1016 | 1.01 | [M + Na − 2H]− | 195.0997 | 9.7 | $C_9H_{18}O_3$ | 2-hydroxy nonanoic acid [CAS: 617-31-2][1] |
| 14 | 14 | 307.2633 | 14.8 | [M + Na − 2H]− | 307.2613 | 6.5 | $C_{18}H_{36}O_2$ | iso-1,2-octadecanediol [PUCHEM: 42607317][1] |
| 16 | 79 | 245.1378 | 0.99 | [M − H] | 245.1389 | −4.5 | $C_{12}H_{22}O_5$ | 3-hydroxyl dodecanoic acid [CAS: 34574-69-1][1] |
| 12 | 80 | 883.5358 | 15.4 | [M − H] | 883.5337 | 2.4 | $C_{47}H_{81}O_{13}P$ | phosphatidylinositol(20:4/18:1) [HMDB: 09901] |
| 11 | 123 | 467.3727 | 14.61 | [M − H]− | 467.3737 | −2.1 | $C_{28}H_{52}O_5$ | 7,9,13-trihydroxyoctacosa-16,22-dienoic acid [USPTO: document #20120136057][1] |
| 9 | 231 | 429.2997 | 11.49 | [M − H] | 429.301 | 1.3 | $C_{27}H_{42}O_4$ | [NA] |
| 13 | 261 | 451.2275 | 1.58 | [M − H]2− | 451.2242 | 7.3 | $C_{40}H_{68}N_6O_{17}$ | [NA] |
|  |  |  |  |  | 451.2249 | 5.8 | $C_{41}H_{64}N_{10}O_{13}$ |  |
|  |  |  |  |  | 451.2305 | −6.6 | $C_{40}H_{64}N_{12}O_{12}$ |  |
| 15 | 620 | 129.0909 | 1.14 | [M − H] | 129.0916 | −2.1 | $C_7H_{14}O_2$ | [NA] |

The serous ovarian cancer metabolites can include cortisone, lysophatidylinositol (18:1), aspartyl-glutamic acid, 16-(6-butoxy-3-hydroxy-4,5-dimethylcyclohex-1-en-1-yl)-6,10-dihydroxy-2,6,10,14-tetramethyl hexadecanoicacid, ceramide, lysophosphatidylethanolamine (22:6), 2-hydroxyl nonanoic acid, iso-1,2-octadecanediol, 3-hydroxyl dodecanedioic acid, phosphatidylinositol (20:4/18:1), and 7,9,13-trihydroxyoctacosa-16,22-dienoic acid.

The serous ovarian cancer metabolites can include the metabolite 1, which has an average m/z of about 552.2 and an average retention time of about 0.7 minutes on a 2.1 mm by 50 mm C-18 column with 1.7 μm particle size when eluted on a gradient with a water:methanol solution of 80% to 10% from 0-15 minutes and 15-23 minutes at 10%. Metabolite 1 can also be described based on the fragmentation ion pattern shown in Table 6.

The serous ovarian cancer metabolites can include the metabolite 6, which has an average m/z of about 365.3 and an average retention time of about 17 minutes on a 2.1 mm by 50 mm C-18 column with 1.7 μm particle size when eluted on a gradient with a water:methanol solution of 80% to 10% from 0-15 minutes and 15-23 minutes at 10%. Metabolite 6 can also be described based on the fragmentation ion pattern shown in Table 6

The serous ovarian cancer metabolites can include the metabolite 9 which has an average m/z of about 429.3 and an average retention time of about 11.5 minutes on a 2.1 mm by 50 mm C-18 column with 1.7 μm particle size when eluted on a gradient with a water:methanol solution of 80% to 10% from 0-15 minutes and 15-23 minutes at 10%. Metabolite 9 can also be described based on the fragmentation ion pattern shown in Table 6

The serous ovarian cancer metabolites can include the metabolite 13, which has an average m/z of about 451.2 and an average retention time of about 1.6 minutes on a 2.1 mm by 50 mm C-18 column with 1.7 μm particle size when eluted on a gradient with a water:methanol solution of 80% to 10% from 0-15 minutes and 15-23 minutes at 10%. Metabolite 13 can also be described based on the fragmentation ion pattern shown in Table 6.

The serous ovarian cancer metabolites can include the metabolite 15, which has an average m/z of about 129.1 and an average retention time of about 1.1 minutes on a 2.1 mm by 50 mm C-18 column with 1.7 μm particle size when eluted on a gradient with a water:methanol solution of 80% to 10% from 0-15 minutes and 15-23 minutes at 10%. Metabolite 15 can also be described based on the fragmentation ion pattern shown in Table 6.

With identification of the serous ovarian cancer metabolites, another level of accuracy can be added to the claimed method by providing a calibration sample. The method can then further include the steps of calibrating the method to align and correctly assign the retention times on a device that the sample is being tested with. The calibration can occur prior to the measurement of a serum sample, or prior to the measurement of multiple serum samples. The calibration can occur during the initial set up and testing of a device upon which the serum samples will be tested. Specifically, the method can include the steps of calibrating the method prior to a measurement of a serum sample or multiple serum samples, wherein the calibration is conducted by testing a device with a calibration sample.

The calibration sample can include at least 3 compounds selected from the group consisting of cortisone, lysophatidylinositol (18:1), aspartyl-glutamic acid, 16-(6-butoxy-3-hydroxy-4,5-dimethylcyclohex-1-en-1-yl)-6,10-dihydroxy-2,6,10,14-tetramethyl hexadecanoic acid, ceramide, lysophosphatidyl ethanolamine (22:6), 2-hydroxyl nonanoic acid, iso-1,2-octadecanediol, 3-hydroxyl dodecanedioic acid, phosphatidylinositol (20:4/18:1), and 7,9,13-trihydroxyoctacosa-16,22-dienoic acid. The calibration sample can include at least 4 compounds selected from the group consisting of cortisone, lysophatidylinositol (18:1), aspartyl-glutamic acid, 16-(6-butoxy-3-hydroxy-4,5-dimethylcyclohex-1-en-1-yl)-6,10-dihydroxy-2,6,10,14-tetramethyl hexadecanoicacid, ceramide, lysophosphatidyl ethanolamine (22:6), 2-hydroxyl nonanoic acid, iso-1,2-octadecanediol, 3-hydroxyl dodecanedioic acid, phosphatidylinositol (20:4/18:1), and 7,9,13-trihydroxyoctacosa-16,22-dienoic acid. The calibration sample can include at least 5 compounds, or at least 6 compounds, or at least 7 compounds selected from the group consisting of cortisone, lysophatidylinositol (18:1), aspartyl-glutamic acid, 16-(6-butoxy-3-hydroxy-4,5-dimethylcyclohex-1-en-1-yl)-6,10-dihydroxy-2,6,10,14-tetramethyl hexadecanoic acid, ceramide, lysophosphatidyl ethanolamine (22:6), 2-hydroxyl nonanoic acid, iso-1,2-octadecanediol, 3-hydroxyl dodecanedioic acid, phosphatidylinositol (20:4/18:1), and 7,9,13-trihydroxyoctacosa-16, 22-dienoic acid. In some embodiments, the sample can include cortisone, ceramide, and aspartyl-glutamic acid. In some embodiments, the sample can include cortisone, lysophatidylinositol (18:1), ceramide, and aspartyl-glutamic acid.

The method can also include preparing the serum sample prior to testing, including the steps of precipitating protein from a blood sample with methanol to make a supernatant and precipitate, separating the protein from supernatant by centrifugation, mixing the supernatant with water and freezing drying the sample, and reconstituting with mobile phase solution at the time of analysis.

The serous ovarian cancer metabolites are compared on a concentration basis versus a control group. The control can be a serum sample taken from a group of patents that do not have ovarian cancer. The control can be collected and tested in conjunction with the measurements of serous OC samples. The control can be an external value to which the serous OC samples are compared, in which each is controlled for the concentration value.

Several key advantages and benefits are supplied to the patient population and medical community with the application of this method. As noted above, ovarian cancer is a difficult disease to detect early, but mortality rates of late stage ovarian cancer are not good. The method provides a key tool in the fight against late stage ovarian cancer by allowing for the detection of early stage cancer based simply on a blood draw of a patient. Thus, another embodiment of the disclosure is a method for eliminating a patient's risk of late stage serous ovarian cancer. The method for eliminating a patient's risk of late stage serous ovarian cancer includes the steps of collecting a serum sample during a patient's health examination, measuring the serum sample for the concentration of each of ten or more of serous OC metabolites 1 through 16, and comparing the concentration of the serous OC metabolites 1 through 16 to the concentration of the same metabolites in an unaffected control sample to determine the presence or absence of serous ovarian cancer. If cancer is detected, then the patient can be prescribed a treatment regime. By monitoring patients for ovarian cancer on a regular basis, early stage ovarian cancers can be detected with greater than 90% accuracy, or with greater than 90% accuracy, greater than 90% sensitivity, and greater than 90% specificity, and the risk of late stage ovarian cancer can be eliminated.

Each of the embodiments listed above are then incorporated into the method for eliminating a patient's risk of late stage serous ovarian cancer.

Another advantage applied to the patient population and medical community is the ability to avoid invasive surgery. With detection via a blood sample, surgery to biopsy a tissue or to explore if a growth is present can be avoided, which can reduce costs and hospital stays, and avoid other risks associated with a surgical procedure. An embodiment of the disclosure can then include a non-invasive method for treating serous ovarian cancer, including the steps of identifying the presence of serous ovarian cancer in a patient and treating the patient with a cancer chemotherapy and/or radiation without resorting to invasive surgical exploration. The step of identifying the presence of serous ovarian cancer can include the steps of obtaining a serum sample from the patient, measuring in the serum sample the concentration of serous OC metabolites 1 through 16, and evaluating the change in the concentrations for the serous OC metabolites 1 through 16 versus a control sample. Each of the embodiments listed above are then incorporated into the non-invasive method for treating serous ovarian cancer.

Another advantage applied to the patient population and medical community is the ability to identify candidates or chemotherapy and/or surgery that eliminates cancerous ovarian tissue. This could include the ability to identify candidates for a drug treatment trial, e.g. a Phase III clinical trial, particularly for candidates that are only in an early stage of serous ovarian cancer. The embodiment of the disclosure can then be a method of identifying candidates for chemotherapy and/or surgery to eliminate cancerous ovarian tissue including the steps of collecting a serum sample during a patient's annual health examination, measuring in the serum sample the concentration of each of ten or more of serous OC metabolites 1 through 16, comparing the concentration of the serous OC metabolites 1 through 16 to the concentration of the same metabolites in an unaffected control sample to determine the presence or absence of serous ovarian cancer, and recommending the candidate for chemotherapy and/or surgery to eliminate the cancerous tissue. Each of the embodiments listed above are then incorporated into the method of identifying candidates for chemotherapy and/or surgery to eliminate cancerous ovarian tissue.

EXAMPLES

Chemicals.

Ultrapure water with 18.2 M$\Omega$ cm resistivity (Barnstead Nanopure UV ultrapure water system, USA) was used to prepare all mobile phase components. Chromasolv® (Fluka) LC-MS grade methanol was purchased from Sigma-Aldrich Corp. (St. Louis, Mo., USA). Lysophatidylinositol (18:1) and ceramide (d18:1/16:0) were purchased from Avanti Polar Lipids, Inc. (Alabaster, Ala., USA).

Sample Preparation.

All samples were collected after informed consent under approved IRB protocols. Serum samples were thawed on ice, and protein precipitation was performed by the addition of methanol in a 3:1 volume ratio to 50 µL of serum. Aliquots of 10 µL from each sample were combined to create a pooled sample, which was split into 50 µL portions before protein precipitation. Samples were vortex-mixed for 10 s and centrifuged at 13,000 g for 7 min. After centrifugation, 150 µL of supernatant was mixed with 400 µL of ultrapure water prior to solvent removal using a VirTis benchtop freeze dryer (Warminster, Pa.). Samples were stored at −80° C. until analysis. Samples were separated into 8 batches with equal representation of epithelial ovarian cancer (EOC) and control samples from each collection site in each group. All samples were thawed, reconstituted with 80:20 (v:v) $H_2O$:MeOH, and analyzed in duplicate. Samples were run in alternating fashion so that duplicate runs for a specific sample were not consecutive. Pooled quality control serum samples were analyzed every eight sample runs. The mass spectrometer was mass calibrated before analysis; and solvent, sample preparation blanks, and pooled samples were analyzed jointly with the EOC and control samples.

UPLC-MS. UPLC-MS was performed using a Waters ACQUITY Ultra-Performance LC system (Waters Corporation, Manchester, UK), fitted with a Waters ACQUITY UPLC BEH C18 column (2.1×50 mm, 1.7 µm particle size), coupled to a high-resolution accurate mass Synapt G2 high-definition mass spectrometry system (Waters Corporation, Manchester, UK). The Synapt G2 HDMS is a hybrid quadrupole-ion mobility-orthogonal acceleration time-of-flight instrument with a typical resolving power of 20,000 FWHM and mass accuracy of 9 ppm at m/z 544.2615. The instrument was operated in negative ion mode with a probe capillary of 2.0 kV and a sampling cone voltage of 35 V. The source and desolation temperatures were 150 and 500° C., respectively, and the nitrogen desolvation flow rate was 1000 L h$^{-1}$. The mass spectrometer was calibrated across the range of m/z 50-1200 using a 0.5 mM sodium formate solution prepared in 90:10 (v/v) 2-propanol:water. Data were mass corrected during acquisition using a leucine enkephalin reference spray (LockSpray) infused at 3 μL min$^{-1}$. Data were acquired in the 50-1200 m/z range, and the scan time was set to 1 s. Data acquisition and processing were carried out using MassLynx V4.1 and MZmine V2.0, respectively. The chromatographic method for sample analysis involved elution with ultrapure water (mobile phase A) and methanol (mobile phase B) using the following gradient program: 0-15 min 80-10% A; 15-23 min 10% A. The flow rate was constant at 0.40 mL min$^{-1}$ for 23 min. The gradient was returned to its initial conditions with a solvent blank run of 11 min. The column temperature was set to 60° C., the autosampler tray was set to 5° C., and the injection volume was 8 μL. UPLC-MS/MS experiments were performed by acquiring mass spectra with applied voltages between 5 and 50 V in the trap cell, using ultra high purity grade argon (>=99.999%) as the collision gas.

Figure 2:
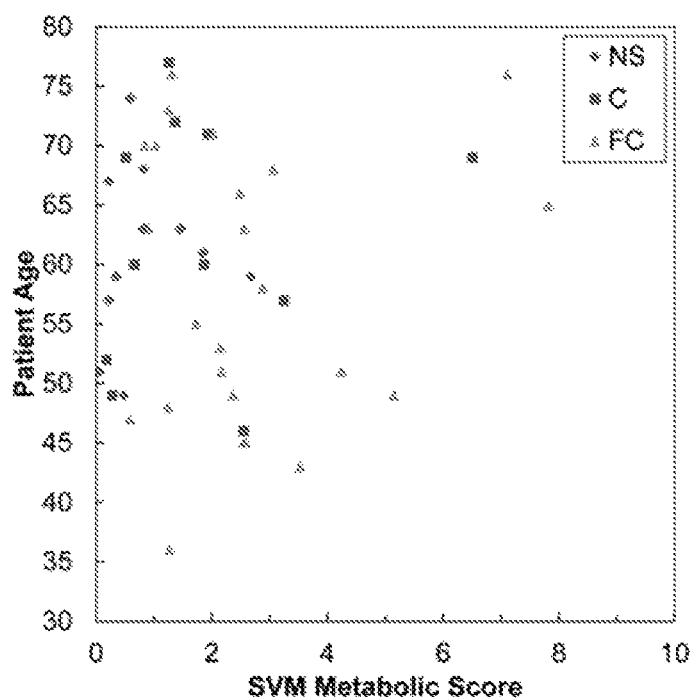
FIG. 2 illustrates the SVM metabolic score of patients from a variety of backgrounds, in accordance with an exemplary embodiment of the disclosure.

Samples were collected from 46 early stage (I/II) serous epithelial ovarian cancer (EOC) patients and 49 age-matched normal healthy controls. Table 3A shows the histopathologies of the patients. The FIGO stage and grade (when available) are list for the cancer patients (normal samples also listed), as is the location. NS=Northside Hospital Atlanta, Ga., USA; C=Alberta Health Services, Alberta, Canada; FC=Fox Chase Cancer Center Biosample Repository Facility, Philadelphia, Pa., USA. The average age of EOC patients at blood draw was 59.7 years old (median=60 years) and the average age of control patients was 56.9 years old (median=55). The difference in average ages was not significant by T test, as shown in FIG. 2. Table 3B shows the ages and locations of a control group.

TABLE 3A

| Patient ID | Ovarian Histopathology | FIGO Stage/ grade | Age at Blood Draw | Source |
|---|---|---|---|---|
| 1117 | Papillary serous carcinoma | 2B/3 | 68 | NS |
| 1105 | Papillary serous carcinoma | 1C/1 | 67 | NS |
| 989 | Papillary serous carcinoma | 1B/3 | 51 | NS |
| 876 | Papillary serous carcinoma | 2A/1 | 63 | NS |
| 550 | Papillary serous carcinoma | 2A/2 | 49 | NS |
| 517 | Papillary serous carcinoma | 1A/3 | 59 | NS |
| 491 | Papillary serous carcinoma | 1/unk | 74 | NS |
| 336 | Papillary serous carcinoma | 1C/3 | 63 | NS |
| 317 | Papillary serous carcinoma | 1C/3 | 59 | NS |
| 170 | Papillary serous carcinoma | 2A/2 | 57 | NS |
| 2 | Papillary serous carcinoma | 2B/3 | 61 | NS |
| RT42 | Papillary serous carcinoma | 1C/unk | 69 | C |
| F5223 | Papillary serous carcinoma | 2C/3 | 52 | C |
| RT68 | Papillary serous carcinoma | 2C/3 | 46 | C |
| RT332 | Papillary serous carcinoma | 1A/1 | 49 | C |
| NEO1 | Papillary serous carcinoma | 1C/unk | 71 | C |
| RT514 | Papillary serous carcinoma | 1C/3 | 57 | C |
| RT965 | Papillary serous carcinoma | 2A/unk | 60 | C |
| RT523 | Papillary serous carcinoma | 1C/3 | 77 | C |
| RT261 | Papillary serous carcinoma | 2A/3 | 72 | C |
| RT36 | Papillary serous carcinoma | 1B/3 | 69 | C |
| RT01 | Papillary serous carcinoma | 2C/3 | 60 | C |
| 106220 | Papillary serous carcinoma | 1C/3 | 58 | FC |
| 108403 | Papillary serous carcinoma | 2C/unk | 76 | FC |
| 111079 | Papillary serous carcinoma | 1A/1 | 47 | FC |
| 113885 | Papillary serous carcinoma | 2C/2 | 53 | FC |
| 115403 | Papillary serous carcinoma | 2C/3 | 55 | FC |
| 116804 | Papillary serous carcinoma | 1C/2 | 68 | FC |
| 118020 | Papillary serous carcinoma | 2A/3 | 51 | FC |
| 119189 | Papillary serous carcinoma | 2C/3 | 51 | FC |
| 119652 | Papillary serous carcinoma | 1A/2 | 43 | FC |
| 120136 | Papillary serous carcinoma | 1A/1 | 49 | FC |
| 122955 | Papillary serous carcinoma | 2C/3 | 45 | FC |
| 123534 | Papillary serous carcinoma | 2C/3 | 66 | FC |
| 124093 | Papillary serous carcinoma | 2B/3 | 63 | FC |
| 125989 | Papillary serous carcinoma | 1C/3 | 49 | FC |
| 126530 | Papillary serous carcinoma | 2B/3 | 70 | FC |
| 127366 | Papillary serous carcinoma | 2C/3 | 70 | FC |
| 127305 | Papillary serous carcinoma | 2B/3 | 71 | FC |
| 131043 | Papillary serous carcinoma | 1A/3 | 76 | FC |
| 128426 | Papillary serous carcinoma | 2B/unk | 36 | FC |
| 129614 | Papillary serous carcinoma | 1C/unk | 45 | FC |
| 130196 | Papillary serous carcinoma | 2B/3 | 65 | FC |
| 131589 | Papillary serous carcinoma | 2C/3 | 48 | FC |
| 133011 | Papillary serous carcinoma | 2C/3 | 63 | FC |
| 135520 | Papillary serous carcinoma | 2C/3 | 73 | FC |

TABLE 3B

| Patient ID | Age at Blood Draw | Source |
|---|---|---|
| 1094 | 50 | NS |
| 1080 | 49 | NS |
| 1064 | 63 | NS |
| 1051 | 45 | NS |
| 917 | 49 | NS |
| 908 | 78 | NS |
| 875 | 47 | NS |
| 783 | 52 | NS |
| 757 | 84 | NS |
| 755 | 75 | NS |
| 751 | 60 | NS |
| 691 | 70 | NS |
| 682 | 53 | NS |
| 677 | 68 | NS |
| 665 | 84 | NS |
| 645 | 61 | NS |
| 636 | 71 | NS |
| 627 | 59 | NS |
| 615 | 42 | NS |
| 593 | 58 | NS |
| 592 | 48 | NS |
| 557 | 61 | NS |
| 544 | 49 | NS |
| 540 | 59 | NS |
| 534 | 72 | NS |
| 504 | 48 | NS |
| 494 | 51 | NS |
| 481 | 63 | NS |
| 479 | 55 | NS |
| 448 | 63 | NS |
| 440 | 50 | NS |
| 1043 | 52 | NS |
| 1046 | 49 | NS |
| 1022 | 58 | NS |
| 960 | 43 | NS |
| 899 | 45 | NS |
| 891 | 52 | NS |
| 873 | 62 | NS |
| 870 | 40 | NS |
| 849 | 64 | NS |
| 842 | 70 | NS |
| 838 | 79 | NS |
| 482 | 44 | NS |
| 719 | 55 | NS |
| 648 | 50 | NS |
| 572 | 40 | NS |
| 524 | 45 | NS |

TABLE 3B-continued

| Patient ID | Age at Blood Draw | Source |
|---|---|---|
| 522 | 61 | NS |
| 505 | 42 | NS |

Negative ion mode UPLC-MS interrogation of the serum metabolome resulted in the detection of >4000 spectral features ($R_t$, m/z pairs). After filtering and curation to remove inconsistent and/or ambiguous features, a remaining pool of 255 was used to build a discriminant linear support vector machine (SVM) model that was evaluated by leave-one-out cross-validation (LOOCV)[9]. Binary classifications (cancer/normal) were established through a previously described "metabolic score" decision function that numerically separates the predicted cancer (positive score) from control (negative score) samples[10] Table 4 lists the 255 metabolic features ($R_t$, m/z pairs) used to build a discriminant linear support vector machine (SVM) model to distinguish sera from epithelial ovarian cancer patients vs. normal controls.

TABLE 4

| Feature | m/z, $R_t$ |
|---|---|
| 342 | 125.0960, 1.81 |
| 284 | 125.0963, 1.15 |
| 620 | 129.0909, 1.14 |
| 579 | 157.1222, 2.29 |
| 140 | 171.1380, 3.49 |
| 280 | 177.1267, 1.96 |
| 12 | 187.0068, 0.69 |
| 74 | 187.0962, 0.72 |
| 378 | 187.0965, 0.99 |
| 438 | 191.0685, 1.78 |
| 105 | 195.1016, 1.01 |
| 186 | 203.0821, 0.60 |
| 490 | 209.0799, 1.69 |
| 170 | 221.1265, 2.24 |
| 403 | 223.1329, 1.23 |
| 539 | 224.0589, 1.03 |
| 41 | 224.0591, 0.84 |
| 379 | 225.0630, 0.86 |
| 43 | 225.1844, 11.68 |
| 1229 | 226.1802, 6.92 |
| 615 | 227.1161, 2.69 |
| 631 | 229.1243, 1.62 |
| 633 | 231.1115, 2.20 |
| 59 | 238.0751, 0.93 |
| 125 | 239.0879, 0.99 |
| 271 | 241.0859, 1.59 |
| 79 | 245.1378, 0.99 |
| 243 | 251.2001, 12.66 |
| 257 | 253.1349, 3.44 |
| 6 | 253.2165, 13.35 |
| 260 | 254.6201, 2.56 |
| 174 | 254.6201, 2.55 |
| 92 | 255.6277, 3.60 |
| 410 | 259.1540, 1.30 |
| 683 | 261.0727, 1.02 |
| 873 | 265.1466, 8.17 |
| 88 | 265.1469, 7.79 |
| 406 | 267.1231, 1.23 |
| 129 | 271.2271, 12.06 |
| 50 | 273.1678, 1.78 |
| 229 | 275.2002, 12.52 |
| 419 | 279.6111, 2.65 |
| 274 | 280.6188, 3.48 |
| 25 | 281.3435, 14.51 |
| 673 | 282.1439, 1.34 |
| 641 | 283.1511, 1.48 |
| 230 | 285.1231, 3.44 |
| 604 | 287.1854, 2.49 |

TABLE 4-continued

| Feature | m/z, $R_t$ |
|---|---|
| 130 | 289.1625, 1.14 |
| 238 | 291.122, 3.43 |
| 264 | 291.1229, 1.62 |
| 987 | 294.6169, 6.45 |
| 1016 | 295.2259, 10.96 |
| 1648 | 297.1513, 8.52 |
| 319 | 301.2005, 3.53 |
| 84 | 301.2164, 13.13 |
| 639 | 302.1125, 1.62 |
| 285 | 302.1126, 3.46 |
| 8 | 303.2324, 13.76 |
| 35 | 305.2476, 14.28 |
| 14 | 307.2633, 14.80 |
| 16 | 309.2789, 15.31 |
| 1238 | 310.1561, 3.82 |
| 58 | 311.1392, 1.65 |
| 277 | 311.6628, 2.78 |
| 223 | 311.6629, 2.76 |
| 269 | 313.1038, 3.45 |
| 156 | 313.1181, 5.29 |
| 630 | 313.1184, 4.94 |
| 13 | 327.232, 13.71 |
| 581 | 328.1576, 7.52 |
| 571 | 329.1733, 4.81 |
| 15 | 329.2477, 14.13 |
| 107 | 331.1898, 4.89 |
| 10 | 339.2303, 13.54 |
| 83 | 353.1615, 2.12 |
| 64 | 365.3413, 16.97 |
| 55 | 367.1573, 2.95 |
| 546 | 369.1727, 3.31 |
| 70 | 369.1731, 3.98 |
| 547 | 369.1732, 4.57 |
| 429 | 383.1525, 1.84 |
| 611 | 385.1671, 1.32 |
| 418 | 388.2509, 10.70 |
| 121 | 397.2038, 4.10 |
| 608 | 399.2179, 6.36 |
| 132 | 407.2192, 12.29 |
| 149 | 409.2347, 13.18 |
| 114 | 409.2348, 12.96 |
| 952 | 411.4854, 0.65 |
| 564 | 413.1989, 3.23 |
| 71 | 415.3568, 16.88 |
| 231 | 429.2997, 11.49 |
| 27 | 429.373, 17.38 |
| 131 | 433.2348, 12.56 |
| 100 | 433.2349, 12.75 |
| 202 | 435.2508, 13.52 |
| 1086 | 445.3309, 14.72 |
| 96 | 445.3313, 14.75 |
| 599 | 447.1329, 6.11 |
| 159 | 447.3469, 14.92 |
| 127 | 448.3058, 8.04 |
| 181 | 449.3618, 15.14 |
| 261 | 451.2275, 1.58 |
| 541 | 452.2772, 11.89 |
| 19 | 452.2776, 13.23 |
| 478 | 465.3544, 13.11 |
| 123 | 467.3727, 14.61 |
| 241 | 473.3621, 15.10 |
| 124 | 476.2769, 12.71 |
| 24 | 476.2777, 12.81 |
| 180 | 478.2931, 12.29 |
| 31 | 478.2934, 13.50 |
| 161 | 480.3084, 13.18 |
| 138 | 480.3086, 13.05 |
| 32 | 480.3088, 14.23 |
| 128 | 487.2037, 0.69 |
| 401 | 498.2884, 7.37 |
| 535 | 498.9287, 7.46 |
| 569 | 498.9291, 6.99 |
| 29 | 500.2776, 12.81 |
| 62 | 501.3056, 10.35 |
| 295 | 501.3935, 15.57 |
| 351 | 503.4092, 15.94 |
| 204 | 504.3075, 12.64 |
| 148 | 504.308, 12.75 |

TABLE 4-continued

| Feature | m/z, $R_t$ |
|---|---|
| 434 | 506.3255, 13.50 |
| 146 | 508.4724, 17.21 |
| 380 | 508.7409, 0.92 |
| 356 | 515.321, 10.84 |
| 340 | 522.4885, 17.88 |
| 28 | 524.2778, 12.79 |
| 110 | 526.2931, 13.16 |
| 66 | 529.3378, 11.18 |
| 196 | 529.4221, 13.37 |
| 310 | 531.1789, 13.00 |
| 144 | 534.4874, 17.52 |
| 45 | 536.5042, 18.56 |
| 473 | 537.2473, 3.45 |
| 957 | 537.414, 14.59 |
| 102 | 537.4151, 14.63 |
| 113 | 539.43, 14.73 |
| 226 | 539.4301, 14.86 |
| 888 | 540.4332, 14.61 |
| 279 | 552.2327, 0.70 |
| 282 | 555.4542, 16.20 |
| 155 | 557.4571, 17.34 |
| 56 | 557.4572, 16.79 |
| 875 | 558.4605, 16.80 |
| 360 | 561.487, 18.22 |
| 188 | 564.5352, 20.55 |
| 189 | 573.4520, 14.90 |
| 207 | 575.4655, 16.44 |
| 198 | 575.4663, 15.99 |
| 201 | 577.4813, 16.47 |
| 108 | 581.4537, 13.82 |
| 137 | 582.5082, 18.53 |
| 76 | 585.4853, 14.50 |
| 337 | 588.4387, 16.84 |
| 309 | 591.3911, 14.54 |
| 171 | 591.4614, 14.89 |
| 48 | 593.4776, 15.28 |
| 154 | 595.2876, 10.10 |
| 34 | 595.4929, 15.49 |
| 256 | 595.7483, 0.71 |
| 286 | 597.3029, 10.89 |
| 267 | 599.3189, 11.64 |
| 531 | 601.7721, 0.74 |
| 329 | 605.4535, 13.78 |
| 175 | 614.4536, 17.10 |
| 206 | 616.4699, 18.09 |
| 33 | 617.732, 0.65 |
| 82 | 619.2874, 10.13 |
| 90 | 620.5979, 18.20 |
| 668 | 627.3723, 7.62 |
| 157 | 634.6114, 21.26 |
| 364 | 642.4857, 18.36 |
| 1011 | 645.4488, 18.46 |
| 381 | 646.6128, 19.47 |
| 213 | 646.6128, 19.27 |
| 160 | 657.4957, 17.10 |
| 795 | 671.4638, 19.04 |
| 798 | 673.4798, 20.42 |
| 195 | 673.4802, 20.36 |
| 884 | 673.7984, 0.77 |
| 1030 | 685.5277, 18.36 |
| 450 | 688.4908, 18.53 |
| 512 | 695.4644, 18.83 |
| 37 | 696.7672, 0.67 |
| 93 | 698.5111, 19.98 |
| 789 | 698.5113, 20.14 |
| 63 | 698.5568, 17.85 |
| 355 | 699.4957, 21.18 |
| 461 | 700.5245, 21.60 |
| 1270 | 714.5073, 19.07 |
| 78 | 716.522, 20.439 |
| 1542 | 720.4897, 18.71 |
| 22 | 722.5133, 19.74 |
| 251 | 723.4963, 20.93 |
| 217 | 724.5256, 20.72 |
| 91 | 724.527, 20.44 |
| 338 | 726.5389, 22.56 |
| 655 | 726.5422, 22.65 |
| 413 | 729.4412, 12.38 |
| 304 | 731.312, 0.69 |
| 583 | 736.5267, 21.06 |
| 344 | 736.5268, 20.86 |
| 232 | 736.5269, 20.94 |
| 388 | 738.507, 18.37 |
| 81 | 738.5073, 19.05 |
| 786 | 740.5231, 19.53 |
| 72 | 740.5232, 19.38 |
| 312 | 742.5382, 21.16 |
| 42 | 742.5386, 21.24 |
| 779 | 742.5397, 21.59 |
| 185 | 744.562, 17.85 |
| 135 | 746.5117, 19.07 |
| 776 | 746.5122, 19.57 |
| 21 | 746.5127, 19.54 |
| 350 | 747.5636, 18.10 |
| 18 | 748.5287, 20.25 |
| 199 | 750.5408, 20.57 |
| 1138 | 750.5433, 21.99 |
| 46 | 750.5438, 22.41 |
| 291 | 757.4730, 12.99 |
| 492 | 760.5257, 20.46 |
| 709 | 760.5299, 20.40 |
| 773 | 762.5069, 18.77 |
| 311 | 762.5071, 18.28 |
| 780 | 764.522, 19.37 |
| 307 | 764.5221, 19.83 |
| 39 | 764.5237, 19.28 |
| 20 | 766.5394, 21.07 |
| 339 | 768.5528, 22.29 |
| 69 | 772.5287, 20.02 |
| 785 | 772.5293, 20.07 |
| 415 | 772.5457, 13.17 |
| 858 | 774.5432, 20.88 |
| 73 | 774.5442, 22.12 |
| 192 | 774.5639, 13.45 |
| 796 | 788.5223, 19.12 |
| 783 | 790.5372, 21.11 |
| 57 | 790.5396, 20.88 |
| 470 | 804.5555, 18.66 |
| 54 | 833.5196, 15.26 |
| 67 | 835.5352, 15.56 |
| 47 | 857.5197, 15.25 |
| 122 | 859.5345, 15.41 |
| 193 | 860.6111, 17.58 |
| 2009 | 861.5512, 15.71 |
| 211 | 863.5657, 16.15 |
| 80 | 883.5358, 15.40 |
| 77 | 887.5679, 15.96 |
| 182 | 909.5515, 15.67 |

Data Processing/Analysis.

Metabolic features (retention time ($R_t$), m/z pairs) were extracted from chromatograms using MZmine V2.0 software and Excel. A five point Savitzky Golay smoothing function was applied to each scan of the raw data prior to peak detection. After chromatogram alignment, the subsequent peak list was conservatively filtered by elimination of peaks that were not present in at least 40 of the 237 collected runs prior to gap filling. The exported peak areas for each sample were normalized by division of the total peak area sum for that sample in Excel. Potential features in which the slope of the peak area of the pooled samples vs. time changed more than one standard deviation away from zero were removed from the peak list. The potential features list was further constrained by purging features that were not present in 50% of sample groups (all samples, EOC samples, or control samples) at ten times the baseline, defined as the maximum peak area observed in the sample blank and ten mobile phase runs (one from each day of analysis). The duplicate sample peak areas were averaged to create a matrix containing sample peak areas for each feature (average $R_t$, average m/z).

The data set was scrutinized for the presence of experimental and instrument bias with principal component analysis (PCA) using MATLAB R2012b (Version 8.0.0.783 The MathWorks, Inc., Natick, Mass., USA) and the PLS Toolbox (v.6.71, Eigenvector Research, Inc., Wenatchee, Wash., USA). Peak area data were labeled with the corresponding collection day, analysis batch, or sample origin. Data were preprocessed by autoscaling, and PCA run with leave-one-out cross-validation. Sample clustering was assessed with the plot of the first versus second principal component.

Linear support vector machine (SVM) analysis of the feature matrix was performed with in-house-developed code utilizing liblinearSVM[25]. Recursive feature elimination (RFE) was used to find the minimum set of discriminant features that maximized accuracy in the classification[9]. For a binary classification problem, linearly-separable samples represented as a row vector x, had membership of two classes g (=N or C), where N stands for normal or control patient samples and C represents EOC disease patient samples with class value c (=−1 for class N, and +1 for class C). The decision function that separated the two classes, defined here as the "EOC metabolic score", was as follows:

$$EOC \text{ metabolic score} = b + \sum_{j=1}^{j} w_j x_{ij} \quad [1]$$

where w and b are the weight and bias parameters that were determined from the training set and J is the total number of features. The sign of the EOC metabolic score determined which class a sample was assigned to: class N if negative and class C if positive. In this classification function, the two classes were divided in the dataspace by a hyperplane'+=0 that maximized the margins between samples of different classes. The margin between the two classes was defined such that:

$$wx''+b \geq 1, c=+1 \quad [2]$$

$$wx'+b \leq -1, c=-1 \quad [3]$$

The RFE method involved an "outer" matrix with 95 columns (equal to the number of serum samples) and 255 rows (equal to the number of features). Each row in the outer matrix represents a subset of features to be tested for discriminatory power. Each subsequent row examines a feature subset that contains one less feature than the previous row. For each row, a set of 95 "inner" matrices is constructed, each one containing a subset of samples to build an SVM model and one sample left out for testing, following standard LOOCV practice. After model building, the SVM feature weights were calculated for each inner matrix, and these weights were summed across the inner matrix. The average feature weight was then calculated across the outer matrix row. The least important feature was then discarded. This process was subsequently repeated for every outer matrix row. A panel of optimal features was determined by examining which feature set had maximized accuracy, sensitivity, and specificity. Data were preprocessed by autoscaling the features across the samples prior to SVM-RFE.

Orthogonal partial least squares discriminant analysis (oPLS-DA[9]) was performed to inspect data after discriminant feature selection via SVM-RFE. oPLS-DA models were internally cross validated using leave-one-out, venetian blinds (10 data splits and 10 samples per blind), contiguous block (10 splits), or random subsets (10 data splits and 10 iterations) approaches. Permutation testing was performed by randomizing the class labels for all samples. Data were preprocessed by autoscaling the features' peak areas across the samples.

Figure 3A:
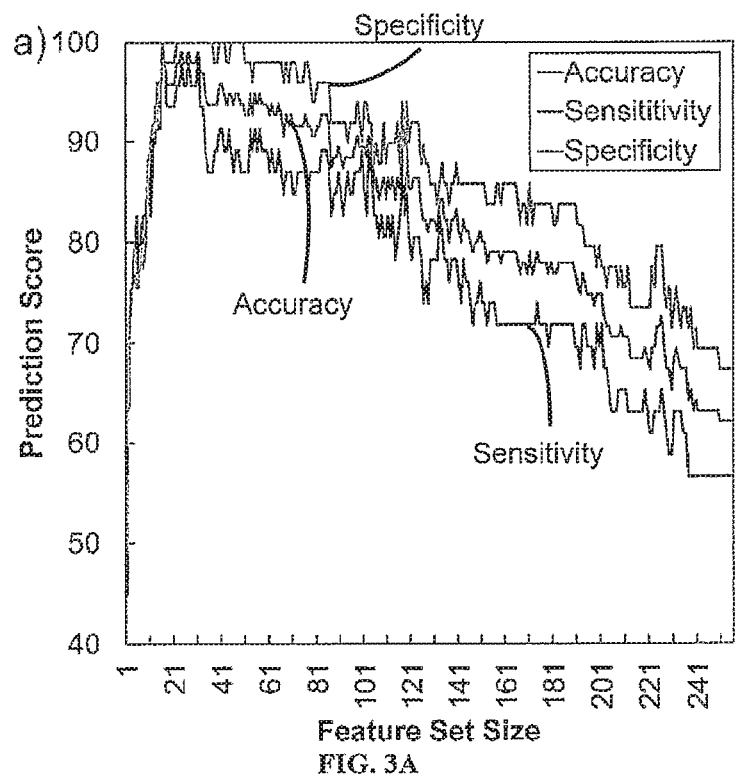
FIG. 3A illustrates specificity, accuracy, and sensitivity based on the size of the feature set.
Figure 3B:
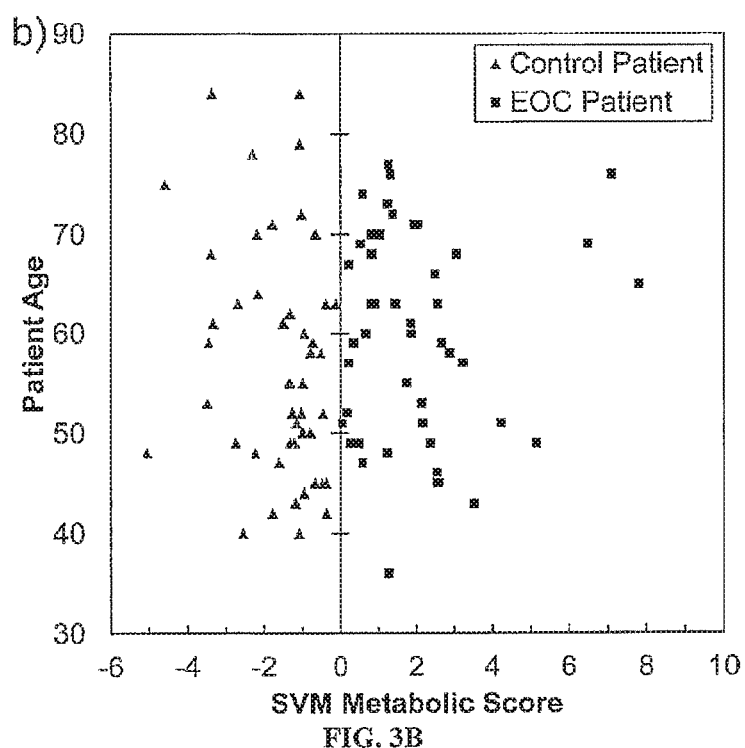
FIG. 3B illustrates the SVM metabolic score for EOC patients and control patients plotted by patient age in accordance with an exemplary embodiment of the disclosure.
Figure 4:
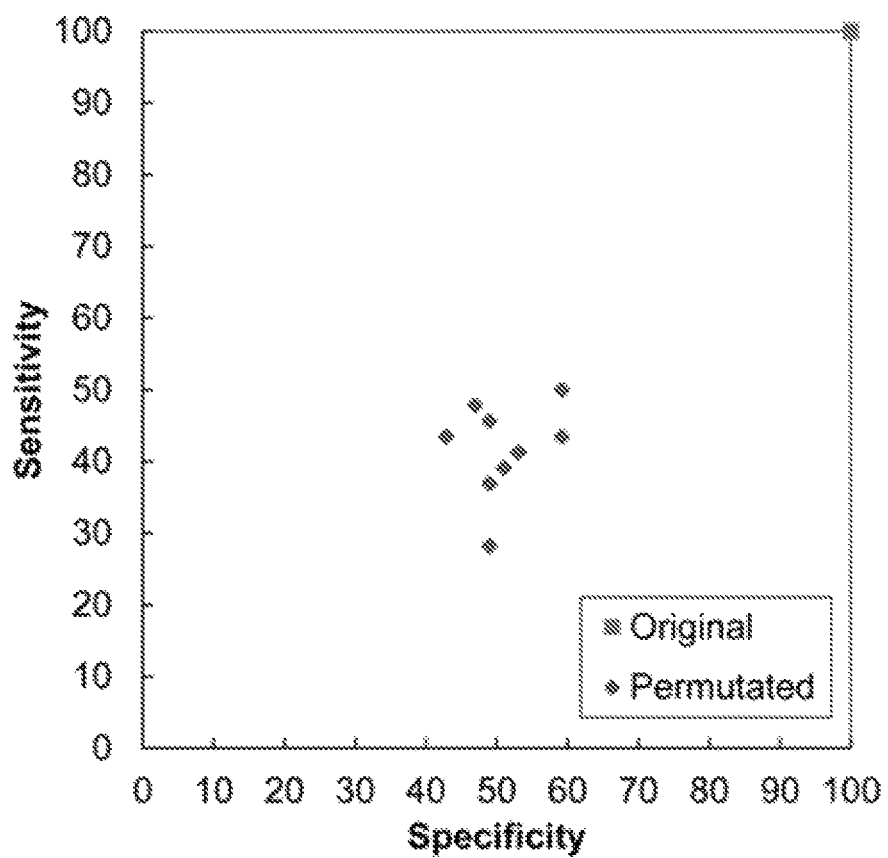
FIG. 4 illustrates a plot of sensitivity versus specificity, in accordance with an exemplary embodiment of the disclosure.

Using all 255 metabolic features, a first SVM model was generated displaying moderate predictive accuracy (accuracy 62%; specificity 57%; sensitivity 67%). Since SVM models built upon large datasets typically contain uninformative features, a number of feature selection methods have been developed to identify subsets with optimal predictive accuracy[11]. A previously described recursive feature elimination (RFE) method[9] was employed to select features that distinguished the early-staged EOC samples from controls with optimal accuracy. FIG. 3A demonstrates the recursive feature elimination (RFE) for selecting 16 metabolic features that distinguish early stage serous epithelial ovarian cancer (EOC) serum samples with high accuracy. As shown in the FIG. 3A, 100% accuracy (100% sensitivity, and 100% specificity) was obtained with a minimum of 16 features. FIG. 3B demonstrates optimal separation between EOC and control samples achieved by the method. The X-axis is the optimal weight vector of the SVM model; the Y-axis is the age of donors (EOC patients or normal control women at the time of sample collection). The vertical line is the projection of the separating hyperplane generated by the SVM model. The discriminant linear SVM model was evaluated by leave-one-out cross-validation (LOOCV). FIGS. 2 and 4 also support the effectiveness of this method. FIG. 2 displays SVM scores plotted as a function of patient age for each of three patient collection sites, and shows there is no clustering of patients based on collection site. FIG. 4 shows a permutation test (n=10) for SVM model built to incorporate the 16 selected features. The class labels were randomized prior to building the SVM models. Plot of sensitivity versus specificity illustrates the class label dependence. The significant separation between the original and permutated data points indicates that the original model was not overfit.

The high predictive accuracy of these 16 metabolites was independently validated by orthogonal partial least squares-discriminant analysis (oPLS-DA) using a variety of cross-validation approaches. oPLS-DA models built with the SVM-RFE selected 16 features incorporating different cross validation (CV) techniques. However, due to limited sample size, data over-fitting is a valid concern. The multivariate SVM-RFA model was thus validated by comparing with oPLS-DA using several cross-validation (CV) approaches, as detailed in the Table 5. Some CV approaches are more stringent than others, but all show consistently high accuracy (>90%). As a negative control, we used a permutation approach showing that when the labels for the samples are scrambled, there is NO classification (i.e. the accuracy drops to 50-60%, which is close to a random object draw). Overall, our results demonstrate that regardless of CV strategy employed we did not find any evidence of over-fitting of the selected metabolite abundances. Techniques include: leave-one-out, venetian blinds (10 data splits and 10 samples per blind), contiguous block (10 splits), and random subsets (10 data splits and 10 iterations). The root mean square error (RMSE) is a measure of performance of how close the data are to the model prediction. RMSE scale is 0 to ∞, with 0 being the best correlation. Similarity of RMSE for the calibration and CV suggests the model is not overfitting the data. For comparison, scores from the permuted set (class labels scrambled) are also included below to demonstrate the oPLS-DA model's dependence on the class labels.

TABLE 5

|  | Accuracy | Sensitivity | Specificity | RMSE EOC | RMSE Control |
|---|---|---|---|---|---|
| oPLS-DA calibration | 1.000 | 1.000 | 1.000 | 0.557 | 0.584 |
| Leave-one-out CV | 0.968 | 0.957 | 0.980 | 0.599 | 0.628 |
| Venetian blinds CV | 0.915 | 0.891 | 0.939 | 0.622 | 0.627 |
| Contiguous block CV | 0.915 | 0.891 | 0.939 | 0.599 | 0.625 |
| Random subsets CV | 0.947 | 0.933 | 0.961 | 0.603 | 0.629 |
| oPLS-DA calibration with label permutation | 0.658 | 0.816 | 0.500 | 0.696 | 0.673 |
| Leave-one-out CV with label permutation | 0.521 | 0.694 | 0.348 | 0.781 | 0.751 |

Figure 5A:
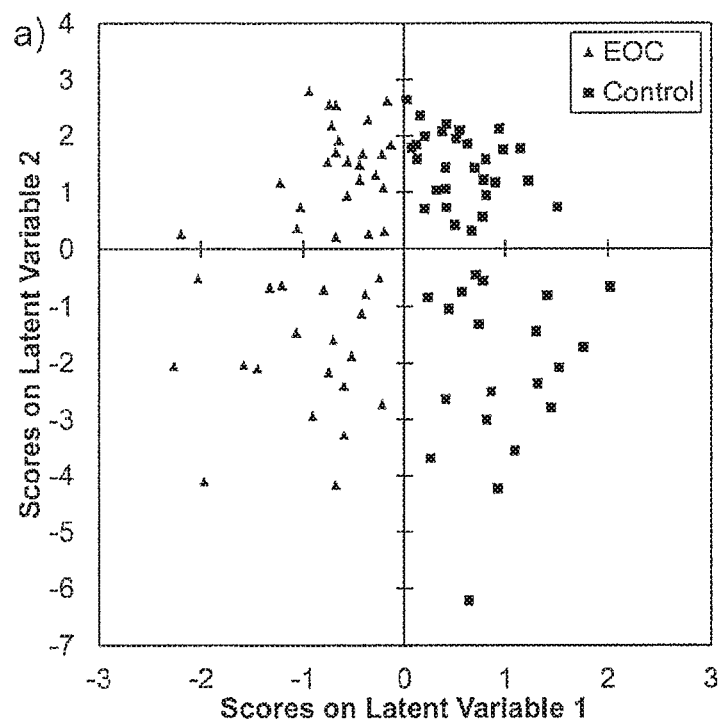
FIG. 5A illustrates a comparison of latent variable scores for EOC versus control patients.
Figure 5B:
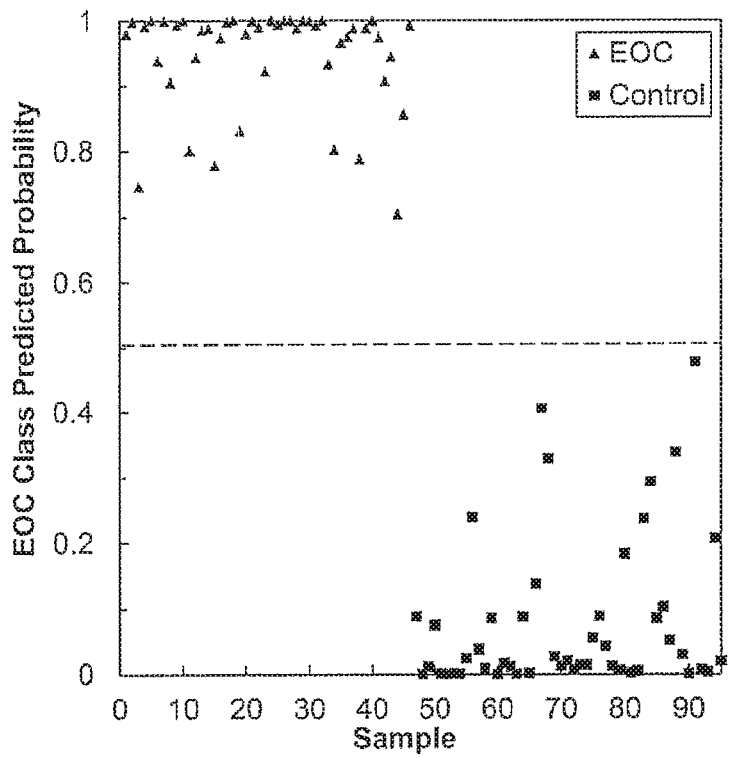
FIG. 5B illustrates the EOC class predicted probability of samples from EOC and control patients, in accordance with an exemplary embodiment of the disclosure.

FIG. 5A and FIG. 5B similarly show the oPLS-DA model built using the selected 16 features identified from SVM-RFE. FIG. 5A shows the score plot of first and second latent variables from the oPLS-DA model built with LOOCV illustrating sample separation into EOC (triangles) and control (square) classes. FIG. 5B shows the predicted probability of EOC class membership, where 1 is most probable and 0 is least likely.

Figure 6:
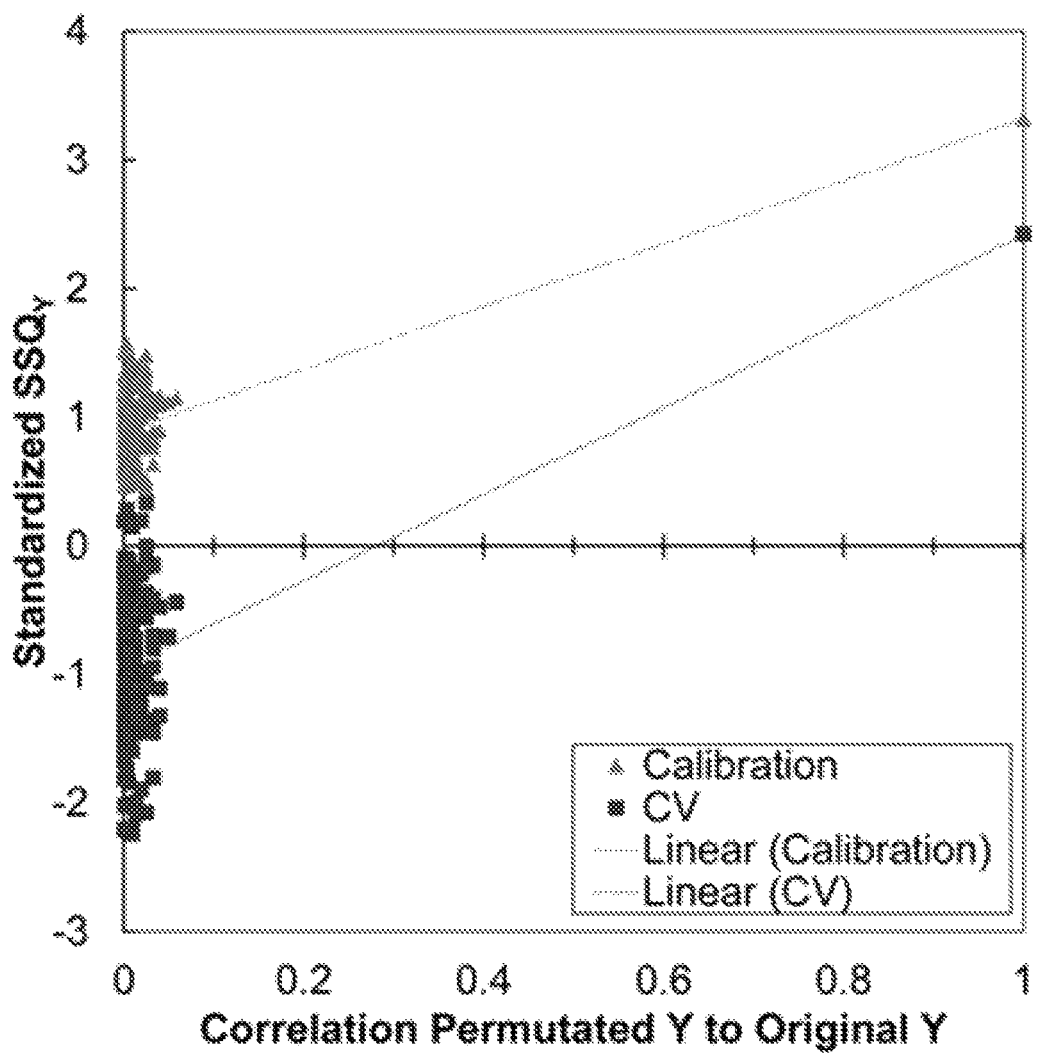
FIG. 6 illustrates a plot of standardized SSQ versus correlation permuted Y to original Y, in accordance with an exemplary embodiment of the disclosure.

Similarly, FIG. 6 shows Y-block permutation results for 200 iterations for both self-predicted (calibration, C) and cross-validated (CV) values. Standardized sum squared Y (SSQY) was plotted versus correlation of permutated results to un-permutated results. The original un-permutated results are shown on the right side of the figure. The significant separation between permutated (left side) and un-permutated (right side) results along with higher y values for the permutated versus the un-permutated results support that the original model is more likely significant, and not overfit.

Metabolite Identification.

Compound identification was carried out for the 16 discriminant features obtained after the feature selection processes. Elemental formulas were generated based on the mass accuracy of the peak of interest and isotopic patterns with a mass error of 10 mDa using MassLynx 4.1. The chemical formulas were searched against the following publically-available databases: Metlin, the human metabolome database (HMDB), Metabolomics Workshop, LIPID Metabolites and Pathways Strategy (LIPID MAPS), and MassBank to determine possible endogenous metabolite candidates. Entries in the MS/MS Metlin database, MassBank, and Lipid Maps, together with literature searches subsequently confirmed the identity of putative candidates. When available, metabolite standards were analyzed to support identification. Identification of metabolites was pursued according to established criteria[26].

The high resolution MS technology employed allowed generation of accurate masses and isotopic patterns for each discriminant feature and therefore establishment of candidate elemental formulas. These proposed metabolite identities were confirmed by UPLC-MS/MS, and the resultant tandem MS spectra were compared to those in databases or literature, resulting in chemical identification of 11 of the 16 discriminating features. Table 2 shown above demonstrated the chemical identification of 16 features that distinguish early staged ovarian cancer seara from the sera of normal healthy controls with high accuracy. Table 6 demonstrates the detailed tandem MS characteristics of the panel for 16 metabolites that distinguish cancer and control samples with optimal accuracy. The fragment ions and the corresponding collision energy (CE) are listed in the table. The selected precursor ions are underlined. Asterisks indicate doubly charged species. The fragments were matched to standards, literature spectra, or were consistent with potential molecular structure. The ions in bold are those matched to standard spectra or literature spectra. Each metabolite was identified according to the following four ID levels: 1) elemental formula, retention time, and MS/MS spectrum of standard matched to feature; 2) MS/MS spectrum consistent with literature spectra and fragmentation ions observed consistent with proposed structure; 3) putative compound class based on chromatographic elution window; and 4) unknown compounds.

TABLE 6

| SerumOC Metabolite # | Feature ID | CE (eV) | m/z of Fragment Ions Observed in MS/MS Experiments | ID Level |
|---|---|---|---|---|
| 1 | 279 | 20 | 827.3548, 809.3323, 747.3443, <u>552.2395</u>*, 543.2249*, 534.2239*, 413.1849*, 273.0027, 259.0977, 241.0892, 184.0645, 167.0386, 127.0412, 113.0359 | 4 |
| 8 | 571 | 20 | <u>329.1796</u>, 311.1724, 301.1815, 176.9747, 149.0667, 137.0574, 122.0354, 109.0600 | 1 |
| 2 | 286 | 30 | <u>597.3027</u>, 417.2384, 315.0561, 281.2487, 241.0145, 152.9943, 78.9543 | 1 |
| 7 | 683 | 20 | 261.0698, 217.0877, 182.0152, 173.9687, 162.0230, 145.0616, 122.0789 | 1 |
| 10 | 226 | 30 | <u>539.4307</u>, 521.4172, 503.3958, 495.4426, 477.4211, 315.2501, 313.2350, 297.2489, 279.2286, 259.1963, 223.1738 | 2 |
| 4 | 45 | 30 | <u>536.5101</u>, 506.5003, 504.4754, 488.4896, 308.3023, 296.2623, 280.2670, 263.2381, 254.2506, 237.2218 | 1 |
| 6 | 64 | 40 | <u>365.3416</u>, 311.1647, 283.2539, 253.0947, 239.0772, 225.0588, 211.0508, 183.0102, 96.9600 | 4 |
| 5 | 28 | 30 | <u>524.2764</u>, 327.2311, 283.2466, 249.1870, 229.1901, 214.0530, 196.0394, 177.1667, 140.0111, 78.9582 | 2 |
| 3 | 105 | 20 | <u>195.1039</u>, 151.1074, 135.0837, 123.0761 | 2 |
| 14 | 14 | 30 | <u>307.2668</u>, 289.2530, 255.2345, 183.0102 | 2 |
| 16 | 79 | 20 | <u>245.1385</u>, 187.0961, 169.0847, 125.0972, 123.0809, 97.0633 | 2 |
| 12 | 80 | 40 | <u>883.5355</u>, 601.2842, 599.3239, 581.3085, 439.2220, 419.2592, 303.2337, 283.2613, 241.0078, 223.0040, 152.9943, 78.9582 | 2 |

TABLE 6-continued

| SerumOC Metabolite # | Feature ID | CE (eV) | m/z of Fragment Ions Observed in MS/MS Experiments | ID Level |
|---|---|---|---|---|
| 11 | 123 | 30 | 467.3770, 449.3589, 423.3873, 405.3660, 297.2414, 279.2286, 263.2381, 251.1994, 223.1607, 215.1610, 187.1320, 169.1188, 141.1308 | 2 |
| 9 | 231 | 40 | <u>429.3003</u>, 411.2852, 305.2087, 277.2086, 123.0809 | 4 |
| 13 | 261 | 20 | 729.3936, 685.3970, 590.2924, 572.2783, 554.2859, 512.2432, <u>451.2338</u>*, 430.2339*, 400.8628, 374.8882, 330.1878, 312.1372*, 286.1901, 276.6193*, 255.6189*, 173.0992, 131.0891 | 4 |
| 15 | 620 | 20 | <u>129.0945</u>, 115.9221, 100.9348, 99.9227 | 4 |

Figure 7:
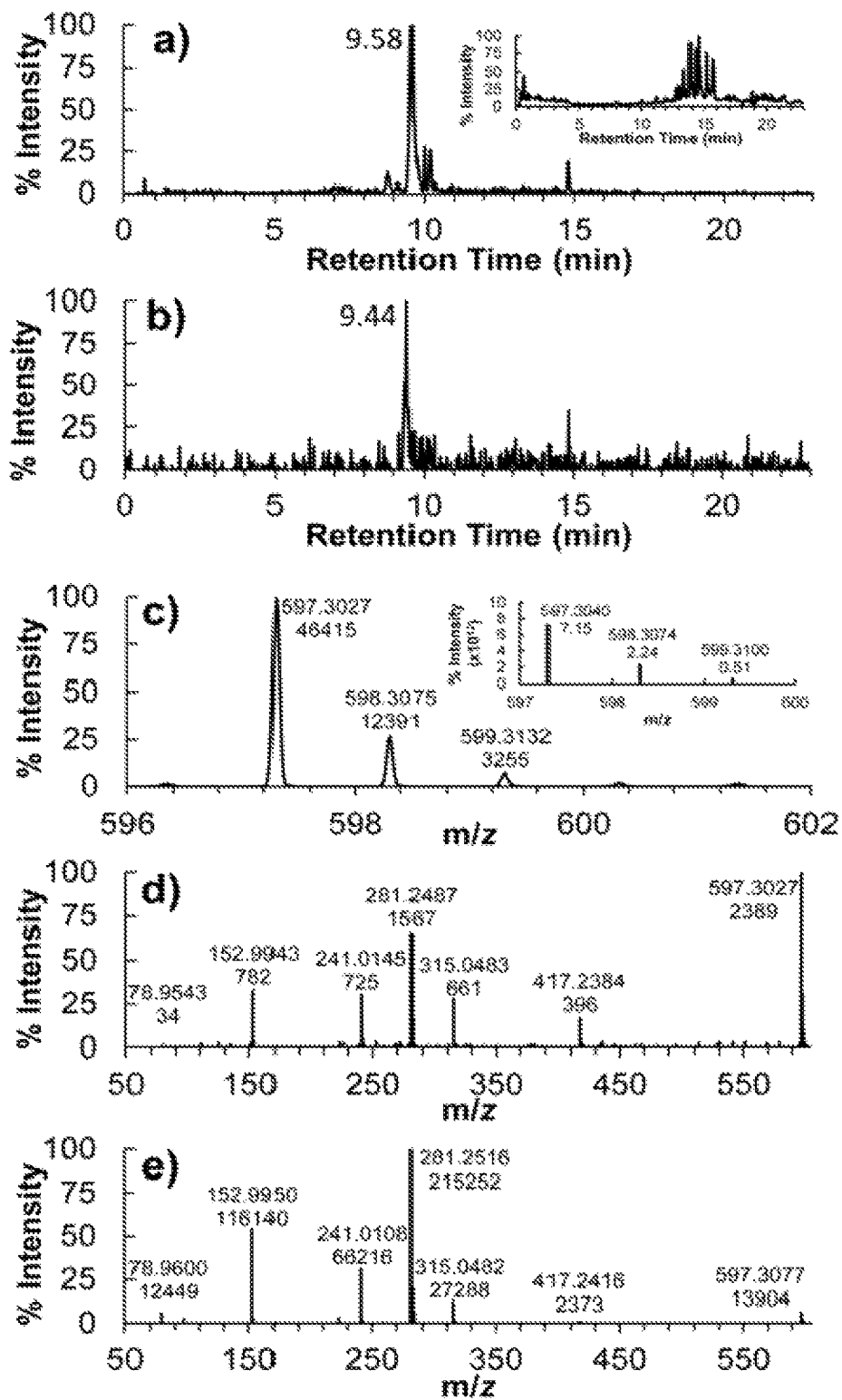
FIG. 7 illustrates retention time chromatographs, mass spectra, and MS/MS spectra of a metabolite, in accordance with an exemplary embodiment of the disclosure.

As an exemplary identification, FIG. 7 demonstrated the identification of metabolite #286 as lysophosposphatidylinositol (18:1). (a) Shows the extracted ion chromatogram of m/z 597.3029 from a pooled serum sample (inset spectrum is total ion chromatogram from a pooled serum sample); (b) extracted ion chromatogram of m/z 597.3029 from a standard; (c) experimental isotopic pattern that agrees with theoretical isotopic pattern for C27H51O12P (see inset spectrum, calculated using MassLynx V4.1); d) MS/MS spectrum from a pooled serum sample collected using a collision energy (CE) of 30 eV; and e) MS/MS spectrum (CE 30 eV) of direct injection of standard.

Many of the identified features were lipids or fatty acids. An emerging body of evidence has implicated changes in lipid and fatty acid metabolism with the onset and progression of ovarian[12] and other types of cancer[13]. In many cases, these changes have been linked to the aberrant expression of genes involved in lipid/fatty acid synthesis. For example, the well-known tumor suppressor gene p53 is mutated in >95% of high-grade serous ovarian cancers[14]. It has recently been reported that the protein encoded by p53 (TP53) interacts with sterol regulatory element-binding proteins (SREBPs) and guanidinoacetate N-methyltransferase (GAMT) resulting in the elevated expression of enzymes involved in fatty acid and cholesterol biosynthesis and the inhibition of fatty acid oxidation leading to lipid anabolism and accelerated tumor growth and progression[15].

Two of the identified metabolites are lysophospholipids (LPLs) [lysophosphatidylethanolamine (LPE) and lysophosphatidylinositol (LPI)]. Serum levels of LPLs have been previously reported to be elevated in OC patients and in matched sets of samples isolated from preoperative vs. postoperative patients[16]. LPIs are also known to bind and activate the orphan G-protein coupled receptor GPR55, which triggers proliferation and anchorage-independent growth of OC cells, as well as activation of Akt and ERK1/2 kinase[17].

Phosphatidylinositol is one of several inositol membrane phospholipids known to be responsible for recruitment of the serine/threonine kinase Akt to the plasma membrane and its subsequent phosphorylation and activation[18]. Phosphorylation of the inositol ring 3'-OH group in inositol phospholipids is carried out by the enzyme phosphatidylinositol 3-kinase (PI3K). A broad range of functions related to cancer onset and progression have been associated with PI3K activity, including proliferation, cell adhesion, apoptosis, and transformation[19]. Our identification of the sphingolipid ceramide as a differentiating metabolite is consistent with its previously proposed roles in ovarian and other cancers[20].

EMBODIMENTS

Additionally or alternatively, the disclosure can include one or more of the following embodiments.

Embodiment 1

A method for detecting serous ovarian cancer, comprising obtaining a serum sample, measuring in the serum sample the concentration of each of ten or more of serous OC metabolites 1 through 16, and evaluating the amount of change in the concentrations for the serous OC metabolites 1 through 16 versus a control sample, wherein an increase for metabolites 1 through 8 and a decrease for metabolites 9 through 16 indicates a positive result for serous ovarian cancer.

Embodiment 2

A method for eliminating a patient's risk of late-stage serous ovarian cancer, comprising collecting a serum sample during the patient's health examination, measuring in the serum sample the concentration of each of ten or more of serous OC metabolites 1 through 16, comparing the concentration of the serous OC metabolites 1 through 16 to the concentration of the same metabolites in an unaffected control sample to determine the presence or absence of serous ovarian cancer, and prescribing a treatment regime for the patient.

Embodiment 3

A non-invasive method for treating serous ovarian cancer, comprising identifying the presence of serous ovarian cancer in a patient, and treating the patient with a cancer chemotherapy and/or radiation without resorting to invasive surgical exploration, wherein identifying the presence of serous ovarian cancer comprising the steps of, obtaining a serum sample from the patient measuring in the serum sample the concentration of serous OC metabolites 1 through 16, and evaluating the change in the concentrations for the serous OC metabolites 1 through 16 versus a control sample.

Embodiment 4

A method of identifying candidates for chemotherapy and/or surgery to eliminate cancerous ovarian tissue comprising collecting a serum sample during a patient's annual health examination, measuring in the serum sample the concentration of each of ten or more of serous OC metabolites 1 through 16, comparing the concentration of the serous OC metabolites 1 through 16 to the concentration of the same metabolites in an unaffected control sample to determine the presence or absence of serous ovarian cancer, and recommending the candidate for chemotherapy and/or surgery to eliminate the cancerous tissue.

Embodiment 5

The methods of one the previous embodiments, wherein the presence or absence of serous ovarian cancer is with greater than 90% accuracy, or greater than 95% accuracy.

Embodiment 6

The methods of one the previous embodiments, wherein the presence or absence of serous ovarian cancer is with greater than 90% accuracy, greater than 90% sensitivity, and greater than 90% specificity, or greater than 95% accuracy, greater than 95% sensitivity, and greater than 95% specificity

Embodiment 7

The methods of one the previous embodiments, where in the concentration of metabolites 1 through 8 increase by a log base 2 value of at least about 0.2 over the control sample, and/or the concentration of metabolites 10 through 16 decrease by a log base 2 value of at least about 0.15 versus the control sample.

Embodiment 8

The methods of one the previous embodiments, wherein the concentration change of the metabolites versus the control sample comprises a log base 2 increase of, about 0.84 for metabolite 1, about 0.70 for metabolite 2, about 0.55 for metabolite 3, about 0.49 for metabolite 4, about 0.34 for metabolite 5, about 0.32 for metabolite 6, about 0.31 for metabolite 7, and about 0.20 for metabolite 8.

Embodiment 9

The methods of one the previous embodiments, wherein the concentration change of the metabolites versus the control sample comprises a log base 2 decrease of about 0.15 for metabolite 10, about 0.25 for metabolite 11, about 0.27 for metabolite 12, about 0.30 for metabolite 13, about 0.31 for metabolite 14, about 0.78 for metabolite 15, and about 1.43 for metabolite 16.

Embodiment 10

The methods of one of the previous embodiments, wherein it further includes the steps of calibrating the method prior to a measurement of a serum sample or multiple serum samples, wherein the calibration is conducted by testing a device with a calibration sample. The calibration sample includes at least 3, at least 4, at least 5, or at least 6 compounds selected from the group consisting of cortisone, lysophatidylinositol (18:1), aspartyl-glutamic acid, 16-(6-butoxy-3-hydroxy-4,5-dimethylcyclohex-1-en-1-yl)-6,10-dihydroxy-2,6,10,14-tetramethyl hexadecanoicacid, ceramide, lysophosphatidyl ethanolamine (22:6), 2-hydroxyl nonanoic acid, iso-1,2-octadecanediol, 3-hydroxyl dodecanedioic acid, phosphatidylinositol (20:4/18:1), and 7,9,13-trihydroxyoctacosa-16,22-dienoic acid.

Embodiment 11

The methods of one the previous embodiments, wherein the metabolites 1 through 16 comprise cortisone, lysophatidylinositol (18:1), aspartyl-glutamic acid, 16-(6-butoxy-3-hydroxy-4,5-dimethylcyclohex-1-en-1-yl)-6,10-dihydroxy-2,6,10,14-tetramethyl hexadecanoicacid, ceramide, lysophosphatidylethanolamine (22:6), 2-hydroxyl nonanoic acid, iso-1,2-octadecanediol, 3-hydroxyl dodecanedioic acid, phosphatidylinositol (20:4/18:1), and 7,9,13-trihydroxyoctacosa-16,22-dienoic acid.

Embodiment 12

The methods of one the previous embodiments, wherein the metabolite 1 has an average m/z of about 552.2 and an average retention time of about 0.7 minutes on a 2.1 mm by 50 mm C-18 column with 1.7 μm particle size when eluted on a gradient with a water:methanol solution of 80% to 10% from 0-15 minutes and 15-23 minutes at 10%; wherein the metabolite 6 has an average m/z of about 365.3 and an average retention time of about 17 minutes on a 2.1 mm by 50 mm C-18 column with 1.7 μm particle size when eluted on a gradient with a water:methanol solution of 80% to 10% from 0-15 minutes and 15-23 minutes at 10%; wherein the metabolite 9 has an average m/z of about 429.3 and an average retention time of about 11.5 minutes on a 2.1 mm by 50 mm C-18 column with 1.7 μm particle size when eluted on a gradient with a water:methanol solution of 80% to 10% from 0-15 minutes and 15-23 minutes at 10%; wherein the metabolite 13 has an average m/z of about 451.2 and an average retention time of about 1.6 minutes on a 2.1 mm by 50 mm C-18 column with 1.7 μm particle size when eluted on a gradient with a water:methanol solution of 80% to 10% from 0-15 minutes and 15-23 minutes at 10%; and/or wherein the metabolite 15 has an average m/z of about 129.1 and an average retention time of about 1.1 minutes on a 2.1 mm by 50 mm C-18 column with 1.7 μm particle size when eluted on a gradient with a water:methanol solution of 80% to 10% from 0-15 minutes and 15-23 minutes at 10%;

Embodiment 4

The methods of one the previous embodiments, where in the metabolite is measured by ultra-performance liquid chromatography with a mass spectrometer as a detector. The chromatographic separation of the metabolites can be conducted for 15 to 40 minutes.

Embodiment 13

The methods of one the previous embodiments, wherein chromatographic separation of the metabolites is conducted on a reverse phase column, including a C8, C18 or C30 column. The chromatographic separation of the metabolites can be conducted using a water:alcohol gradient elution, or a water:methanol gradient elution. The metabolites are separated using a C18 UPLC column with a methanol:water gradient elution, and the metabolites measured by a MS detector.

Embodiment 14

The methods of one the previous embodiments, wherein the serum sample is prepared by the steps of precipitating protein from a blood sample with methanol to make a supernatant and precipitate, separating the protein from supernatant by centrifugation, mixing the supernatant with water and freezing drying the sample, and reconstituting with mobile phase solution at the time of analysis.

Embodiment 15

The methods of one the previous embodiments, wherein the control is a serum sample from a group of patients that do not have ovarian cancer.

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based can be readily utilized as a basis for the design of other structures, methods, and systems for carrying out the several purposes of the embodiments and claims presented in this application. It is important, therefore, that the claims be regarded as including such equivalent constructions.

We claim:
1. A method for detecting serous ovarian cancer comprising:
measuring in a serum sample the concentration of each of ten or more of serous OC metabolites 1 through 16 having neutral elemental formula(s) and identification as associated in Table 1; and

TABLE 1

| Serum OC Metabolite No. | Neutral Elemental Formula | Metabolite Identification |
|---|---|---|
| 1 | $C_{42}H_{80}N_3O_{30}$, $C_{43}H_{76}N_7O_{26}$, $C_{42}H_{76}N_9O_{25}$ | |
| 2 | $C_{27}H_{51}O_{12}P$ | Lysophatidylinositol (18:1) |
| 3 | $C_9H_{18}O_3$ | 2-hydroxyl nonanoic acid |
| 4 | $C_{34}H_{67}NO_3$ | Ceramide (d18:1/16:0) |
| 5 | $C_{27}H_{44}NO_7P$ | Lysophosphatidylethanolamine (22:6) |
| 6 | $C_{24}H_{46}O_2$ | |
| 7 | $C_9H_{13}N_2O_7$ | aspartyl-glutamic acid |
| 8 | $C_{21}H_{28}O_5$ | cortisone |
| 9 | $C_{27}H_{42}O_4$ | |
| 10 | $C_{32}H_{60}O_6$ | 16-(6-butoxy-3-hydroxy-4,5-dimethylcyclohex-1-en-1-yl)-6,10-dihydroxy-2,6,10,14-tetramethyl hexadecanoic acid |
| 11 | $C_{28}H_{52}O_5$ | 7,9,13-trihydroxyoctacosa-16,22-dienoic acid |
| 12 | $C_{47}H_{81}O_{13}P$ | Phosphatidylinositol (20:4/18:1) |
| 13 | $C_{40}H_{68}N_6O_{17}$, $C_{41}H_{64}N_{10}O_{13}$, $C_{40}H_{64}N_{12}O_{12}$ | |
| 14 | $C_{18}H_{36}O_2$ | iso-1,2-octadecanediol |
| 15 | $C_7H_{14}O_2$ | |
| 16 | $C_{12}H_{22}O_5$ | 3-hydroxyl dodecanedioic acid | evaluating the amount of change in the concentrations for at least one of the serous OC metabolites 1 through 16 versus control sample concentrations for the same at least one of the serous OC metabolites 1 through 16 in a control serum sample;

wherein an increase for metabolites 1 through 8 and a decrease for metabolites 9 through 16 indicates a positive result for serous ovarian cancer.

2. The method of claim 1 further comprising obtaining the serum sample;
wherein evaluating the amount of change in the concentrations comprises evaluating the amount of change in the concentrations for all of the serous OC metabolites 1 through 16 versus the control serum sample.

3. The method of claim 2 further comprising calibrating the method prior to a measurement of a serum sample or multiple serum samples;
wherein the calibration is conducted by testing a device with a calibration sample.

4. The method of claim 2 further comprising measuring the metabolite by ultra-performance liquid chromatography with a mass spectrometer as a detector.

5. The method of claim 4, wherein measuring is conducted for 15 to 40 minutes.

6. The method of claim 4, wherein measuring is conducted on a reverse phase column.

7. The method of claim 4, wherein measuring is conducted using a water:alcohol gradient elution.

8. The method of claim 2, wherein the 16 metabolites are separated using a C18 UPLC column with a methanol:water gradient elution; and
wherein the metabolites are measured by a MS detector.

9. The method of claim 2, wherein the concentration of metabolites 1 through 8 increase by a log base 2 value of at least about 0.2 over the control serum sample.

10. The method of claim 2, wherein the concentration of metabolites 10 through 16 decrease by a log base 2 value of at least about 0.15 versus the control serum sample.

11. The method of claim 2, wherein each of the metabolites 1 through 16 are selected from the group consisting of cortisone, lysophatidylinositol (18:1), aspartyl-glutamic acid, 16-(6-butoxy-3-hydroxy-4,5-dimethylcyclohex-1-en-1-yl)-6,10-dihydroxy-2,6,10,14-tetramethyl hexadecanoicacid, ceramide, lysophosphatidylethanolamine (22:6), 2-hydroxyl nonanoic acid, iso-1,2-octadecanediol, 3-hydroxyl dodecanedioic acid, phosphatidylinositol (20:4/18:1), and 7,9,13-trihydroxyoctacosa-16,22-dienoic acid.

12. The method of claim 2, wherein the serum sample is prepared by:
precipitating protein from a blood sample with methanol to make a supernatant and precipitate;
separating the protein from the supernatant by centrifugation;
mixing the supernatant with water and freeze drying the sample; and
reconstituting with a mobile phase solution at the time of analysis.

13. The method of claim 2, wherein the control serum sample is a serum sample from a group of patients that do not have ovarian cancer.

14. A method for eliminating a patient's risk of late-stage serous ovarian cancer comprising:
collecting a serum sample during the patient's health examination;
measuring in the serum sample the concentration of each of ten or more of serous OC metabolites 1 through 16 having neutral elemental formula(s) and identification as associated in Table 1;

TABLE 1

| Serum OC Metabolite No. | Neutral Elemental Formula | Metabolite Identification |
|---|---|---|
| 1 | $C_{42}H_{80}N_3O_{30}$, $C_{43}H_{76}N_7O_{26}$, $C_{42}H_{76}N_9O_{25}$ | |
| 2 | $C_{27}H_{51}O_{12}P$ | Lysophatidylinositol (18:1) |
| 3 | $C_9H_{18}O_3$ | 2-hydroxyl nonanoic acid |
| 4 | $C_{34}H_{67}NO_3$ | Ceramide (d18:1/16:0) |
| 5 | $C_{27}H_{44}NO_7P$ | Lysophosphatidyl-ethanolamine (22:6) |
| 6 | $C_{24}H_{46}O_2$ | |
| 7 | $C_9H_{13}N_2O_7$ | aspartyl-glutamic acid |
| 8 | $C_{21}H_{28}O_5$ | cortisone |
| 9 | $C_{27}H_{42}O_4$ | |
| 10 | $C_{32}H_{60}O_6$ | 16-(6-butoxy-3-hydroxy-4,5-dimethylcyclohex-1-en-1-yl)-6,10-dihydroxy-2,6,10,14-tetramethyl hexadecanoic acid |
| 11 | $C_{28}H_{52}O_5$ | 7,9,13-trihydroxyoctacosa-16,22-dienoic acid |
| 12 | $C_{47}H_{81}O_{13}P$ | Phosphatidylinositol (20:4/18:1) |
| 13 | $C_{40}H_{68}N_6O_{17}$, $C_{41}H_{64}N_{10}O_{13}$, $C_{40}H_{64}N_{12}O_{12}$ | |
| 14 | $C_{18}H_{36}O_2$ | iso-1,2-octadecanediol |
| 15 | $C_7H_{14}O_2$ | |
| 16 | $C_{12}H_{22}O_5$ | 3-hydroxyl dodecanedioic acid | comparing the concentration of the serous OC metabolites 1 through 16 to the concentration of the same metabolites in an unaffected control serum sample to determine the presence or absence of serous ovarian cancer; and prescribing a treatment regime for the patient.

15. The method of claim 14 further comprising calibrating the device prior to a measurement of a serum sample or multiple serum samples;

wherein the calibration is conducted by testing the device on a calibration sample.

16. The method of claim 14, wherein the concentration of metabolites 1 through 8 increase by a log base 2 value of at least about 0.2 over the control serum sample.

17. The method of claim 14, wherein the concentration of metabolites 10 through 16 decrease by a log base 2 value of at least about 0.15 versus the control serum sample.

18. A non-invasive method for treating serous ovarian cancer comprising identifying the presence of serous ovarian cancer in a patient; and treating the patient with a cancer chemotherapy and/or radiation without resorting to invasive surgical exploration;

wherein identifying the presence of serous ovarian cancer comprises:

obtaining a serum sample from the patient;

measuring in the serum sample the concentration of serous OC metabolites 1 through 16 having neutral elemental formula(s) and identification as associated in Table 1; and evaluating the change in the concentrations for the serous OC metabolites 1 through 16 versus a control serum sample;

TABLE 1

| Serum OC Metabolite No. | Neutral Elemental Formula | Metabolite Identification |
|---|---|---|
| 1 | $C_{42}H_{80}N_3O_{30}$, $C_{43}H_{76}N_7O_{26}$, $C_{42}H_{76}N_9O_{25}$ | |
| 2 | $C_{27}H_{51}O_{12}P$ | Lysophatidylinositol (18:1) |
| 3 | $C_9H_{18}O_3$ | 2-hydroxyl nonanoic acid |
| 4 | $C_{34}H_{67}NO_3$ | Ceramide (d18:1/16:0) |
| 5 | $C_{27}H_{44}NO_7P$ | Lysophosphatidyl-ethanolamine (22:6) |
| 6 | $C_{24}H_{46}O_2$ | |
| 7 | $C_9H_{13}N_2O_7$ | aspartyl-glutamic acid |
| 8 | $C_{21}H_{28}O_5$ | cortisone |
| 9 | $C_{27}H_{42}O_4$ | |
| 10 | $C_{32}H_{60}O_6$ | 16-(6-butoxy-3-hydroxy-4,5-dimethylcyclohex-1-en-1-yl)-6,10-dihydroxy-2,6,10,14-tetramethyl hexadecanoic acid |
| 11 | $C_{28}H_{52}O_5$ | 7,9,13-trihydroxyoctacosa-16,22-dienoic acid |
| 12 | $C_{47}H_{81}O_{13}P$ | Phosphatidylinositol (20:4/18:1) |
| 13 | $C_{40}H_{68}N_6O_{17}$, $C_{41}H_{64}N_{10}O_{13}$, $C_{40}H_{64}N_{12}O_{12}$ | |
| 14 | $C_{18}H_{36}O_2$ | iso-1,2-octadecanediol |
| 15 | $C_7H_{14}O_2$ | |
| 16 | $C_{12}H_{22}O_5$ | 3-hydroxyl dodecanedioic acid. |

19. The method of claim 18 further comprising calibrating the device prior to a measurement of a serum sample or multiple serum samples;

wherein the calibration is conducted by testing the device on a calibration sample.

20. The method of claim 19, wherein the calibration sample includes at least three compounds selected from the group consisting of cortisone, lysophatidylinositol (18:1), aspartyl-glutamic acid, 16-(6-butoxy-3-hydroxy-4,5-dimethylcyclohex-1-en-1-yl)-6,10-dihydroxy-2,6,10,14-tetramethyl hexadecanoicacid, ceramide, lysophosphatidylethanolamine (22:6), 2-hydroxyl nonanoic acid, iso-1,2-octadecanediol, 3-hydroxyl dodecanedioic acid, phosphatidylinositol (20:4/18:1), and 7,9,13-trihydroxyoctacosa-16,22-dienoic acid.

21. The method of claim 18, wherein the concentration of metabolites 1 through 8 increase by a log base 2 value of at least about 0.2 over the control serum sample; and wherein the concentration of metabolites 10 through 16 decrease by a log base 2 value of at least about 0.15 versus the control serum sample.

* * * * *